US012629153B2

(12) United States Patent
Ranallo et al.

(10) Patent No.: US 12,629,153 B2
(45) Date of Patent: May 19, 2026

(54) CINCH LIGATING ASSEMBLY

(71) Applicant: UNITED STATES ENDOSCOPY GROUP, INC., Mentor, OH (US)

(72) Inventors: Cynthia Ann Ranallo, Eastlake, OH (US); Alex Uspenski, Chardon, OH (US); Reza Mohammadpour, Willoughby Hills, OH (US); Christopher J. Kaye, Middleburg Heights, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 202 days.

(21) Appl. No.: 18/326,371

(22) Filed: May 31, 2023

(65) Prior Publication Data

US 2024/0032930 A1 Feb. 1, 2024

Related U.S. Application Data

(63) Continuation of application No. 16/739,636, filed on Jan. 10, 2020, now Pat. No. 11,701,121.

(60) Provisional application No. 62/791,378, filed on Jan. 11, 2019.

(51) Int. Cl.
    *A61B 17/12*     (2006.01)
    *A61B 17/00*     (2006.01)

(52) U.S. Cl.
    CPC ................... *A61B 17/12013* (2013.01); *A61B 2017/00473* (2013.01)

(58) Field of Classification Search
    None
    See application file for complete search history.

(56) References Cited

U.S. PATENT DOCUMENTS 5,334,199 A     8/1994   Yoon
5,431,668 A     7/1995   Burbank, III et al.
            (Continued)

FOREIGN PATENT DOCUMENTS

CN     101112327 A  *  1/2008   ......... A61B 17/1285
CN     104248461 A  *  12/2014   ............. A61B 17/12
            (Continued)

OTHER PUBLICATIONS

International Search Report from PCT/US20/13076 dated Mar. 12, 2020.
            (Continued)

*Primary Examiner* — Shaun L David
(74) *Attorney, Agent, or Firm* — CALFEE, HALTER & GRISWOLD LLP

(57) ABSTRACT

A device and assembly for ligating a target tissue to restrict blood flow to the tissue, where the device is a ligating device that is irreversibly tightened by a cinch component. The device further has a hook to hold the ligating element on a delivery tool. The ligating element can be a continuous loop or can be a clip and can be repositionable until the cinch is used to tighten it. The cinch holds the ligating device on the loop while being positioned, and then secures the ligating device once it is positioned around target tissue to which a user desires to restrict blood flow. A method of using the assembly includes an actuator assembly, drive wire, and pusher element to manipulate the ligating device and cinch component.

7 Claims, 43 Drawing Sheets

(56) References Cited

U.S. PATENT DOCUMENTS

| | | | | |
|---|---|---|---|---|
| 5,490,861 | A * | 2/1996 | Kratsch | A61B 17/00 606/174 |
| 5,766,184 | A * | 6/1998 | Matsuno | A61B 17/122 606/151 |
| 5,855,586 | A | 1/1999 | Habara et al. | |
| 6,010,523 | A * | 1/2000 | Sabin | A61B 10/06 606/208 |
| 7,727,247 | B2 * | 6/2010 | Kimura | A61B 17/1285 606/142 |
| 8,152,822 | B2 | 4/2012 | Gayzik | |
| 11,350,947 | B2 * | 6/2022 | Shi | A61B 17/1285 |
| 11,937,828 | B2 * | 3/2024 | Takizawa | A61B 17/1227 |
| 2001/0021860 | A1 * | 9/2001 | Ouchi | A61B 10/06 606/205 |
| 2002/0045909 | A1 * | 4/2002 | Kimura | A61B 17/083 606/151 |
| 2003/0069592 | A1 * | 4/2003 | Adams | A61B 17/1227 606/142 |
| 2003/0144673 | A1 | 7/2003 | Onuki et al. | |
| 2004/0176784 | A1 | 9/2004 | Okada | |
| 2005/0261709 | A1 | 11/2005 | Sakamoto et al. | |
| 2006/0100645 | A1 | 5/2006 | Kobayashi et al. | |
| 2006/0155308 | A1 * | 7/2006 | Griego | A61B 17/1285 606/142 |
| 2006/0224165 | A1 * | 10/2006 | Surti | A61B 17/29 606/142 |
| 2009/0005792 | A1 | 1/2009 | Miyamoto et al. | |
| 2009/0088778 | A1 | 4/2009 | Miyamoto et al. | |
| 2009/0204125 | A1 | 8/2009 | Onishi et al. | |
| 2009/0326558 | A1 * | 12/2009 | Cui | A61B 17/1227 606/143 |
| 2010/0049218 | A1 | 2/2010 | Miyamoto et al. | |
| 2010/0152753 | A1 * | 6/2010 | Menn | A61B 17/083 606/158 |
| 2011/0054498 | A1 * | 3/2011 | Monassevitch | A61B 17/122 606/157 |
| 2011/0106107 | A1 | 5/2011 | Binmoeller et al. | |
| 2013/0072945 | A1 * | 3/2013 | Terada | A61B 17/1227 606/157 |
| 2013/0123818 | A1 * | 5/2013 | Li | A61B 17/122 606/157 |
| 2015/0190135 | A1 | 7/2015 | Ibrahim et al. | |
| 2020/0008811 | A1 * | 1/2020 | Itoh | A61B 17/1285 |

FOREIGN PATENT DOCUMENTS

| | | |
|---|---|---|
| EP | 1671594 A1 | 6/2006 |
| JP | 2002224124 A | 8/2002 |
| JP | 2007136128 A | 6/2007 |
| WO | 2014181678 A1 | 11/2014 |

OTHER PUBLICATIONS

Office Action from U.S. Appl. No. 16/739,636 dated Feb. 1, 2022.
Office Action from U.S. Appl. No. 16/739,636 dated Aug. 23, 2022.
Notice of Allowance from U.S. Appl. No. 16/739,636 dated Mar. 1, 2023.

* cited by examiner

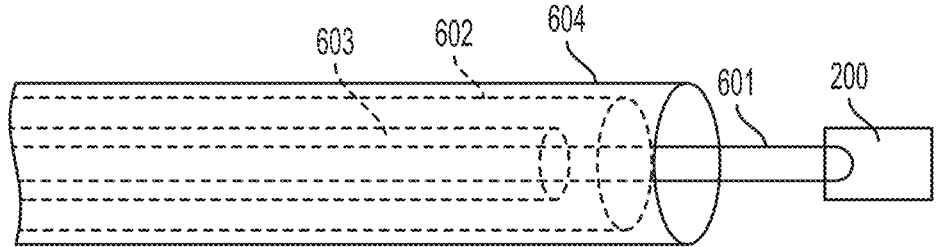
FIG. 8A
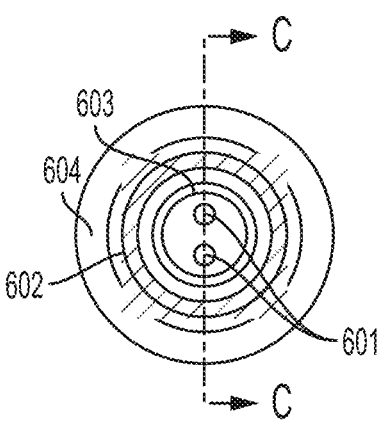
FIG. 8B
FIG. 8C

CINCH LIGATING ASSEMBLY

CROSS-REFERENCE TO RELATED APPLICATIONS

The present application is a continuation of U.S. application Ser. No. 16/739,636, filed Jan. 10, 2020, which claims the benefits of and priority to U.S. Provisional Patent Application No. 62/791,378, filed on Jan. 11, 2019, the entire disclosures of which are incorporated herein by reference.

FIELD OF THE INVENTION

The various embodiments relate to a ligating assembly in general and more particularly to an adjustable ligating element that can be irreversibly tightened once it is positioned around tissue to be removed, such as a polyp. The ligating assembly uses a cinch element to tighten either a loop that can surround the tissue to be ligated or to tighten a clip that can be used to ligate the tissue of interest. The ligating assembly can be used to cut off blood supply to assist in removing tissue but is not limited to such a use.

BACKGROUND INFORMATION

Conventional ligating loops, when cinched around tissue, restrict blood flow to that tissue, which prevents bleeding during removal of the tissue with an electrocautery snare. Common types of tissue removed in this manner include but are not limited to a pedunculated polyp, which is stalk-like in structure. In a pedunculated polyp, the stalk provides blood flow to a larger section of abnormal tissue. Ligating loops can also be used on larger lesions such as gastric lesions or to close defects.

Traditional ligating loop devices rely on an outer catheter sheath that is moved independently from the handle mechanism typically used to extend and retract devices from the sheath. In such devices, the handle mechanism irreversibly releases or cinches the loop instead of extending or retracting it. This design allows for inadvertent release or cinching of the ligating loop, unnecessarily complicating its use for physicians and nurses. Improvements to conventional ligating loops may be made to reduce the risk of such unintentional deployment and/or cinching. Similar improvements can be made to conventional clip deployment devices that rely on bendable or frangible components to cinch and release a clip, that can be a ligating clip.

SUMMARY OF THE INVENTION

In view of the foregoing, one or more embodiments of a device for ligating tissue to reduce and/or eliminate blood flow to the tissue include a ligating element, a hook, and a cinch component. The ligating element attaches to a hook on the distal end of a drive wire. The hook can be releasably connected to the proximal end of the ligating element. The cinch component can be configured to retain the hook in connection with the ligating element when the ligating device is in a first configuration and configured to cinch the ligating element around a target tissue and expose the hook in a second configuration. When the hook is exposed, as in the second configuration, the exposed hook is detachable from the ligating element. The ligating element can be a loop made of a polymer (and/or glass fiber or other fibrous element) that can be placed around a target tissue to restrict its bloodflow. Alternatively, instead of a loop, the hemostatic element can comprise a clip used to compress target tissue either to prevent or staunch blood flow. The cinch component can be adjacent to a distal end of a pusher tube. The pusher tube and the drive wire can extend longitudinally through the catheter sheath such that the ligating element and the cinch component extend outward from a distal end of the catheter. The catheter can have an actuator assembly at the proximal end of the catheter. The cinch component can have a proximal portion for retaining the hook and a distal portion for irreversibly cinching the ligating device. Distal movement of the cinch component exposes the hook and permits it to be removed from the ligating device.

The actuator assembly at the proximal end of the catheter in an exemplary embodiment can have a first and second handle releasably attached to each other, where movement of the first and second handles together moves the ligating element, cinch component, and hook positioned in the first configuration, and where distal movement of the second handle separate from the first handle causes the ligating element, cinch component, and hook to be in the second configuration. Further, connecting the first and second handles together removes the hook from the ligating element.

A method of deploying a tissue ligating element according to one or more embodiments can include the steps of extending a ligating element having a proximal end removably connected to a hook at a distal end of a drive wire out of a catheter sheath by moving a pusher tube and a drive wire in a distal direction; tightening the ligating element and exposing the hook by sliding a cinch component at a distal end of the pusher tube over the ligating element by moving the pusher tube distally, and releasing the ligating element by removing the hook from the ligating element. The method according to the exemplary embodiments herein also allows for repositioning the ligating element by moving the pusher tube and drive wire together in proximal or distal directions as needed to achieve the proper location around the target tissue. The cinch component can have a distal portion configured to tighten the ligating element, and a proximal portion configured to retain the hook on the ligating element. The cinch component can also have a feature on the proximal portion to ensure retaining of the hook prior to deployment. The cinch component may be assembled from more than one part or produced as a single part. The drive wire can have a proximal end connected to a first handle and the pusher tube comprises a proximal end connected to a second handle.

Further, the steps of extending and repositioning the ligating element, cinch component, and hook can be performed by moving the first and second handles together. The step of tightening the ligating element and exposing the hook is performed by moving the second handle independently of the first handle. The irreversible tightening of the ligating element is configured to restrict bloodflow to the target tissue.

These and other aspects of the exemplary embodiments will become apparent from the following detailed description, taken in conjunction with the accompanying drawings, illustrating by way of example the principles of the various exemplary embodiments.

BRIEF DESCRIPTION OF THE DRAWINGS

In order to facilitate a fuller understanding of the exemplary embodiments, reference is now made to the appended drawings. These drawings should not be construed as limiting, but are intended to be exemplary only.

FIG. 8A depicts a close-up view of the distal ends of the elongate members in accordance with an exemplary embodiment.

FIG. 8B depicts a cross-section view of the elongate members of FIG. 8A in accordance with an exemplary embodiment.

FIG. 8C depicts a cross-section view along line C-C of FIG. 8B.

FIG. 31A illustrates an alternative embodiment of a loop with a supplemented distal end.

FIG. 31B illustrates a view of the loop with supplemented distal end according to the embodiment illustrated in FIG. 31A.

DETAILED DESCRIPTION OF EMBODIMENTS

Figure 1:
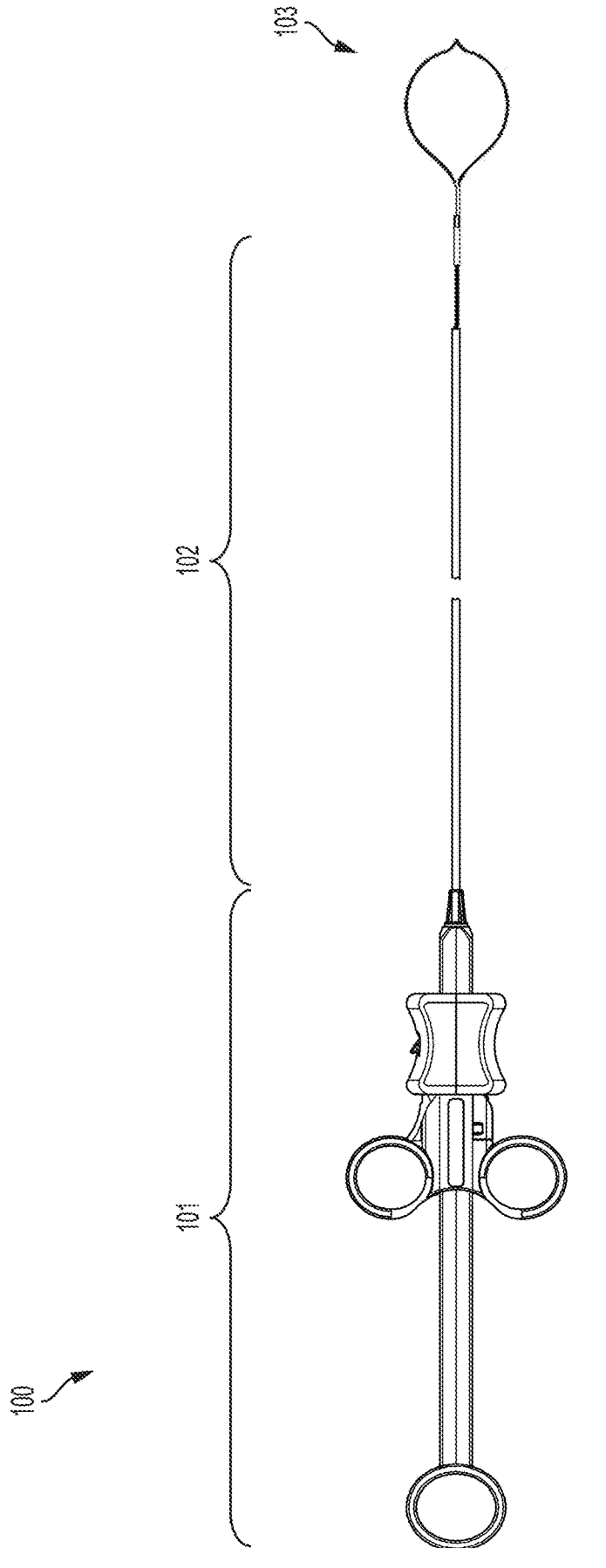
FIG. 1 depicts a ligating device in accordance with an exemplary embodiment.

The following description is intended to convey a thorough understanding of the embodiments by providing various embodiments and details involving a loop and cinch component. Various additional embodiments and details involve a clip and cinch component. It is understood, however, that the invention is not limited to these specific embodiments and details, which are exemplary only. It is further understood that one possessing ordinary skill in the art, in light of known devices, systems and methods, would appreciate the use of the invention for its intended purposes and its benefits in any number of alternative embodiments. Generally speaking, the cinch, the ligating device, and the hook that connects the ligating device to the delivery device can be referred to as a ligating device. The proximal handle and actuating components located at a proximal end of the ligating device can be generally referred to as an actuator apparatus. The ligating device has the components of the exemplary embodiments described herein. The device and method described herein is for a ligator comprised of either a loop or a clip located on the distal end of the device, a stopper or cinch through which the loop or clip is passed, a hook designed to attach to the loop or clip proximal to the cinch, and a drive cable attached to the hook. The cinch component can have a retaining tube attached to it. The retaining tube covers the hook to prevent the loop or clip from being prematurely dislodged. The retaining tube can have a retaining provision on it. Examples of this can be a crimp in the retaining tube, a drawn down portion of the retaining tube, bendable or flexible tabs, or other provisions for increasing retaining force on the hook. The crimp can create inward facing bumps that add to the friction fit. The bendable tabs can be cutouts in the retaining tube that bend inward. Alternatively, a separate component may be added to the proximal portion of the retaining portion to prevent inadvertent movement of the hook from within the retaining portion of the cinch. It could be a washer with a smaller inner diameter than the retaining tube, for example. It can also be a uniformly reduced inner diameter that reduces in size from a first inner diameter to a smaller second inner diameter. This can provide an additional feature, which can be a friction fit, for maintaining the hook in the retaining portion of the cinch while the loop is being adjusted. By having a crimp in the tube, the user of the device can feel the resistance as he or she actively pulls the hook back to move it. This can prevent inadvertent deployment. This extra feature can be located on the proximal portion of the retaining tube, and can be at or near the end.

The cinch component and the retaining tube can be of one piece of material. A pusher tube is located proximal to the cinch retaining member and inside the outer catheter sheath. The pusher tube is used to dislodge the retaining portion of the cinch from the catheter, and can be made from a polymer, such as PEEK, PTFE, or other known polymers, a stainless steel spring coil or braid, a steel or ceramic hypotube with adequate stiffness and flexibility, or a composite polymer steel support structure such that the material has sufficient strength to dislodge the cinch. The pusher tube and the drive cable for the hook are attached to separate slidable elements on the handle. The pusher tube can be connected to the most distal slidable element. The drive cable can be connected to the most proximal slidable element. The pusher tube and the drive cable can be actuatable independently from each other, or can be actuatable dependent on each other. The slidable elements that the pusher tube and drive cable are attached to are designed so that they can be connected to each other and separated by the user. This allows the user to move the ligating loop in and out of the catheter without tightening the cinch or releasing the loop until the user is ready to do so.

A hemostatic clip can also be used at the distal end instead of a loop, and can be operated with the same actuator apparatus and cinch component, as will be described herein.

The loop of the ligating assembly in the exemplary embodiment described herein can be opened and closed in a manner similar to conventional snares by pushing slidable elements in a distal direction to open the loop and a proximal direction to close the loop. In the exemplary embodiment described herein, the loop is deployed only when the user takes an intentional step to deploy it, by disengaging a latch between the two slidable elements to cinch the loop and then re-engaging the two slidable elements to release the loop. The slidable elements can be a spool and a ring handle, as described in the exemplary embodiment herein.

The user can place the loop around the target tissue, and then the user can separate the spool from the ring handle by using a button located on top of the spool. The button can be a protrusion coming from a prong on the ring handle, that is latched on to the spool. Moving the spool (separated from the ring handle) in a distal direction while holding the ring handle in a fixed position advances the pusher tube and cinching assembly so that the cinching assembly tightens the loop around the tissue of interest. Once the cinching assembly is sufficiently tight, the user releases the loop from the catheter by reconnecting the spool to the ring handle. In the clip embodiment, the cinching assembly closes the clip. Once the clip is closed, the user can release the clip from the catheter.

The target tissue of the ligating device can be abnormal tissue that is going to be removed and/or biopsied. The tissue can be abnormal growths such as polyps, and in particular, pedunculated polyps with a stalk-like structure. The tissue can be non-cancerous or cancerous. It can be used in the field of gastroenterology, but is not limited thereto. The ligating device can be a one-time use device that can be repositioned as many times as needed to properly position the loop around the target tissue. The embodiments described herein are not limited to the described target tissue. The clip can be used to ligate tissue or for example, can also be used to secure two portions of tissue together, as may be required to close an opening caused by a surgical incision or other causes.

The ligating device can also be used to close large defects via a "purse string" technique. With the purse string technique, endoscopic clips can be placed around the perimeter of a defect to serve as posts for the ligating loop to close the defect. The operation of the actuator assembly and cinch component for closing large defects can be that as described in the exemplary embodiments herein.

The ligating device can extend through the instrument channel of an endoscope to restrict the blood flow to tissue or to close large defects.

The exemplary embodiment of the device described herein can also be used with a hemostatic clip on the distal end, in place of a ligating loop. The hemostatic clip can be used to close a perforation or fistula, or to stop any type of bleeding in an area accessible by endoscope, such as for example, to stop bleeding by the removal of a polyp or other abnormal tissue growth. The hemostatic clip may also be used to close tissue that has been surgically cut such as during other endoscopic procedures and other fields. Just as with the ligating assembly, the hemostatic clip can be used in the field of gastroenterology, but is not limited thereto. The hemostatic clip can be repositioned as many times as needed to properly position the loop around the target tissue. The release/cinching mechanism allows for reloading of either a loop or clip. The proximal portion of either may be attached to the hook and extended back within the retainer of the cinch in order to connect the end effector to the delivery device. In exemplary embodiments, new clips can be reloaded onto the same delivery device as a cost-saving measure.

Referring to FIG. 1, an endoscopic ligating device 100 is illustrated. This device 100 has an actuator assembly 101 at a proximal end, a catheter sheath assembly 102 in the middle, and a ligating loop 103 at a distal end. Additional figures illustrate close-up views of the components.

Figure 2:
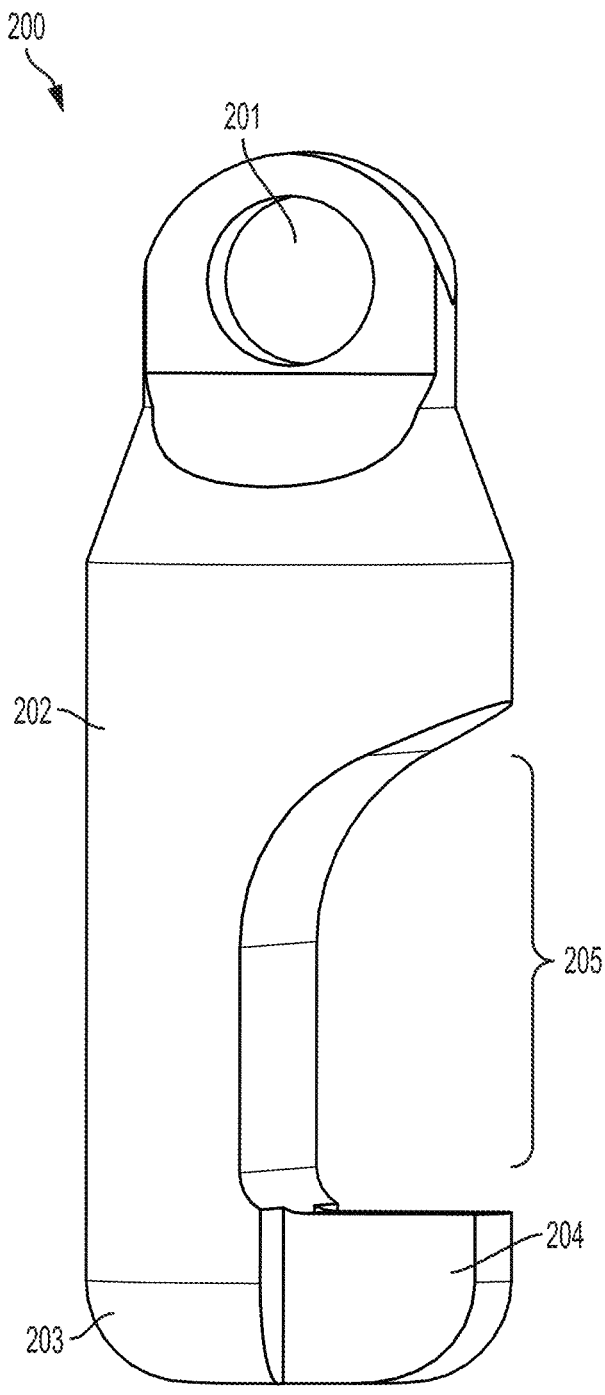
FIG. 2 depicts a hook in accordance with an exemplary embodiment.

At the distal end of the ligating device, there is a hook 200, a cinch component 1000, and a loop 103. FIG. 2 illustrates the hook 200. The hook 200 has an eye 201 at its proximal end, a shank 202, a bend 203, a distal end portion 204, and a gap 205. The bend 203 can be a radius. The eye 201 is intended for a drive wire to be threaded through it. The distal end portion 204 can be a hook shape or flat and is intended for a proximal end of a loop or clip to be hooked onto it. It can have provisions for releasing its hold on the loop 103, or other devices, independent of the handle mechanism such as a spring-loaded retainer that releases the loop 103 once extended out from the catheter sheath 102. The hook 200 can also have provisions for protecting against premature deployment of the loop after the initial deployment of the sheath once the cinch is advanced off the hook.

Figure 3:
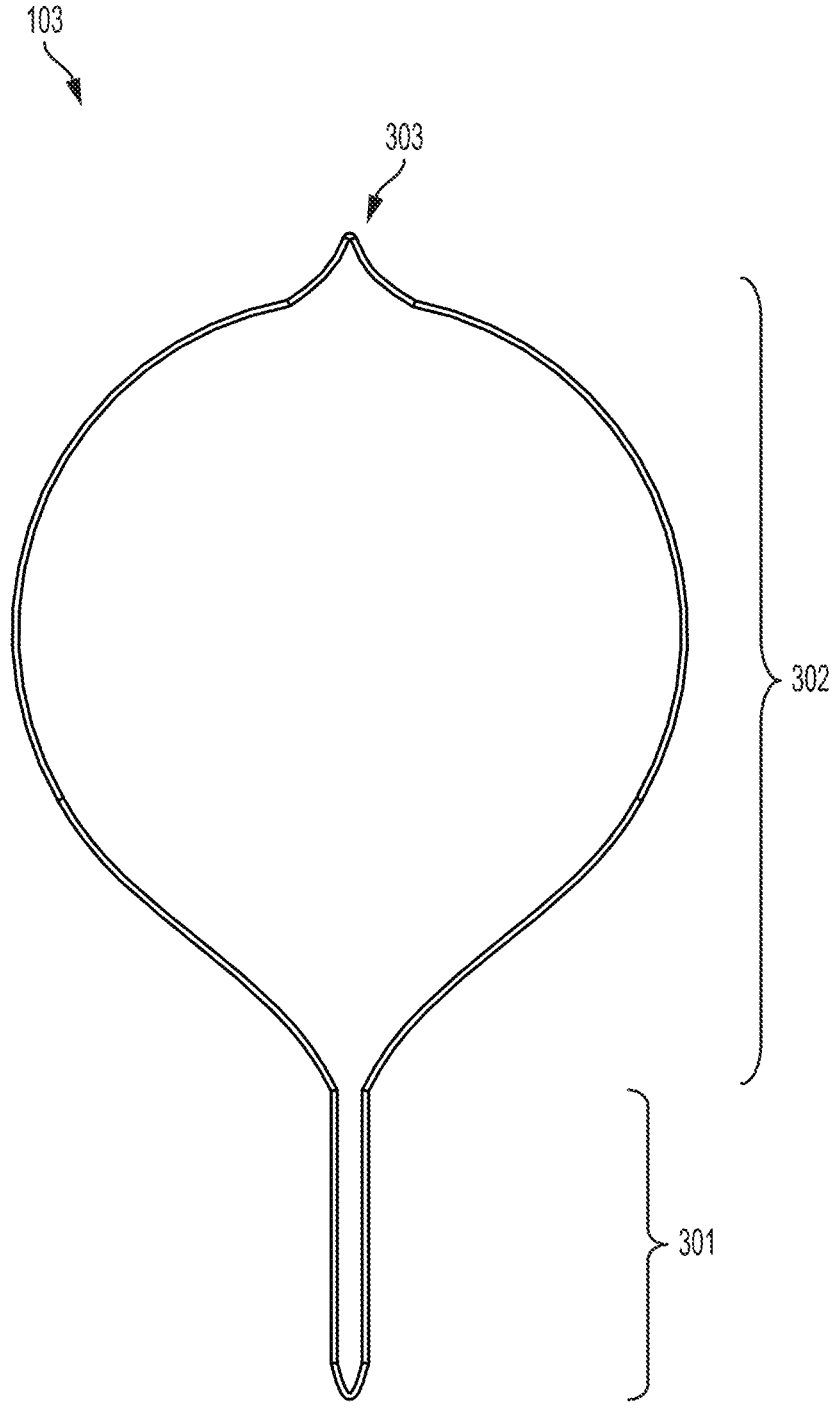
FIG. 3 depicts a loop in accordance with an exemplary embodiment.
Figure 27:
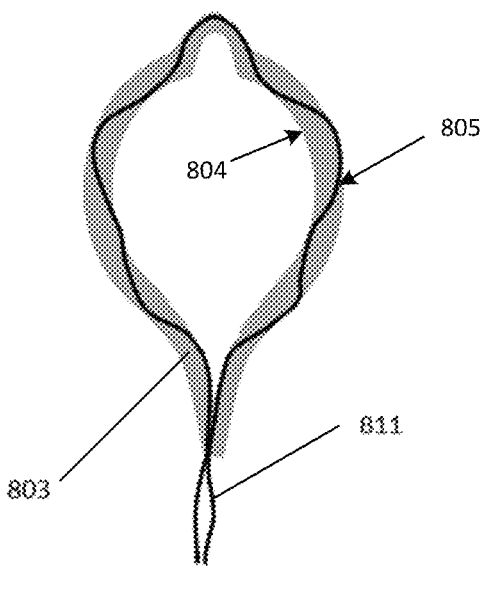
FIG. 27 depicts an alternative embodiment of a loop with an overmolded layer and a core.
Figure 28:
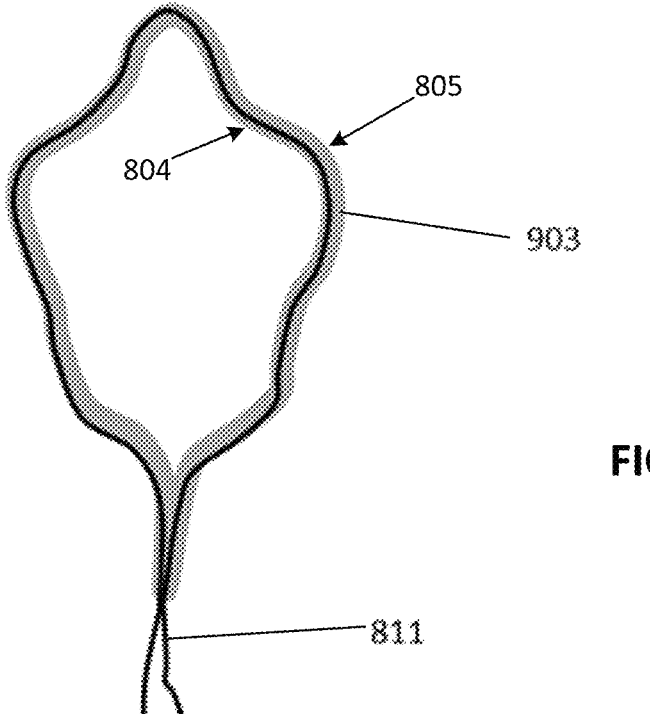
FIG. 28 illustrates another alternative embodiment of a loop with an overmolded layer and a core.

FIG. 3 illustrates the loop 103 in a relaxed position. The loop 103 can be one of many configurations; the loop 103 illustrated in FIG. 3 is exemplary. The loop 103 can have a narrower proximal portion 301 for looping around the distal end portion 204 of a hook 200. The loop can have a wider distal portion 302 of a size and shape capable of being positioned around a polyp. The loop can have a substantially pointed distal tip 303. The loop may be thicker at the distal end with respect to the proximal end. By having a thicker distal end, the loop can have improved stiffness, less traumatic ligating action on the tissue, and a better cinch force can be applied as the cinch is moved distally along the loop. A similar effect can be achieved with features of varying thickness and shape, such as increasing the overall thickness. The loop can be made of nylon. In another exemplary embodiment, the loop can be another polymer, or the loop can be made of a metal with insulation or a non-conductive coating on it. The loop can also be made of a glass or woven fiber that is molded, over-molded, pultruded and/or heat-set, or treated in a manner to give it shape memory characteristics so that it can achieve the desired open geometry for efficient placement and tissue recruitment. The glass or woven fiber produces increased rigidity and surface features that allow it to better grip and recruit the tissue. The loop can be formed by extrusion, pultrusion or woven from polymer or polymer-coated fibers that are heat set to produce the desired geometry. The loop can also be injection molded or over-molded. FIG. 27 illustrates a loop having an overmold 803, that can be molded with a glass-fiber roving or other fiber or woven support core 811 inside the overmold. This core can be a heat-resistant synthetic fiber such as Kevlar, or it can be a non-magnetic, non-conducting metal. The fiber can be pushed to the inner wall 804 and/or outer wall 805 by the polymer flow front, or it can remain centrally located within the overmold 803 of the loop. Rather than being detrimental, having the fiber as part of the outer wall 805 could help grip tissue. FIG. 28 illustrates another exemplary embodiment of loop geometry that can be an overmolded material 903 molded with additional bends and can have glass-fiber roving or other fiber or woven support core 811. Just as with the embodiment in FIG. 27, the loop in FIG. 28 can be Kevlar, or non-magnetic, non-conducting metal. As with the other loop geometry, the fiber as shown may not stay in the center, but may be pushed to the inner and outer wall by the polymer flow front. Having the glass fiber roving or other support core pushed to the side of the overmolding 903 so that it forms part of the exterior surface of the loop can help the loop grip tissue.

Figure 29A:
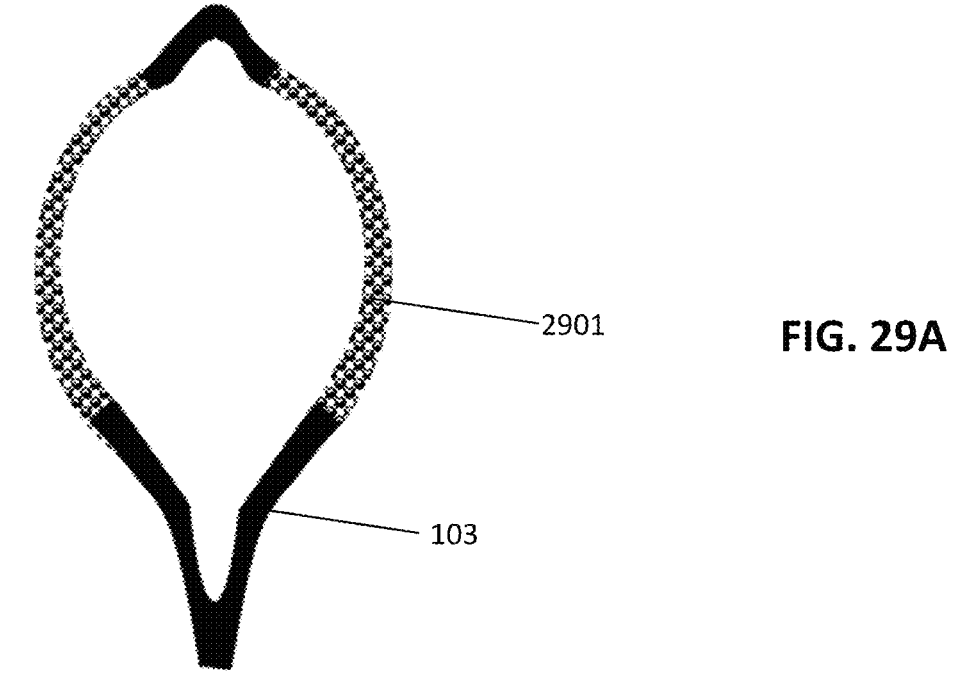
FIG. 29A illustrates another alternative embodiment of a loop having a textured surface on at least a portion of the loop.
Figure 29B:
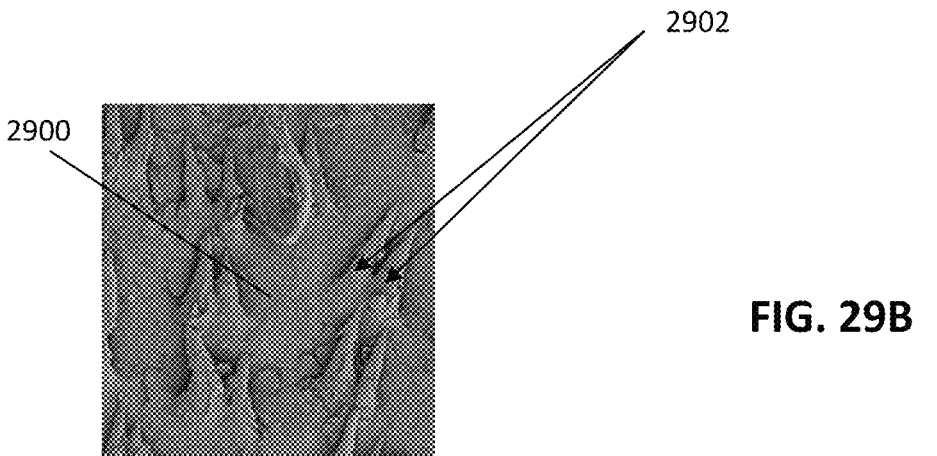
FIG. 29B illustrates a magnified view of horned structures on an anteater's tongue.

Increasing the stiffness of the loop by adding fibers or fiber-like elements to create a modified surface that is not entirely smooth can provide additional grip by the loop on the tissue. In an exemplary embodiment, surface characteristics that mimic those found in nature can be used to enhance the grip of the loop on the tissue. For example, the tongue of an anteater has horned structures on its surface for retaining ants. As another example, a feline tongue has a microstructure to its surface that enhances the capture and movement of fluids. While transporting and capturing fluids can initially appear counterintuitive to increasing a grip on tissue, moving fluid away from the target surface is an effective strategy. Channeling moisture away from the external surface of the loop can facilitate a more efficient tightening of it prior to its desired release. Biomimicry, which is the design and production of materials, structures, and systems that are modeled on biological entities and processes, can be used to provide a textured surface to the loop. FIG. 29A illustrates an exemplary embodiment of the use of biomimicry to enhance the outer surface of the loop. In FIG. 29A, the loop 103 can have a microstructure textured surface 2901 on at least a portion of the loop. FIG. 29B illustrates an exemplary embodiment of a magnification of the microstructure textured surface that the loop can have. FIG. 29B is an example of biomimicry, as it is a magnification of the surface of horned structures 2902 on an anteater's tongue 2900. The microstructure textured surface 2901 of the loop 103 in FIG. 29A is not limited to that of an anteater's tongue, and can be any microstructure textured surface that increases the adherence of the outer surface of the loop to tissue.

Figures 30A, 30B:
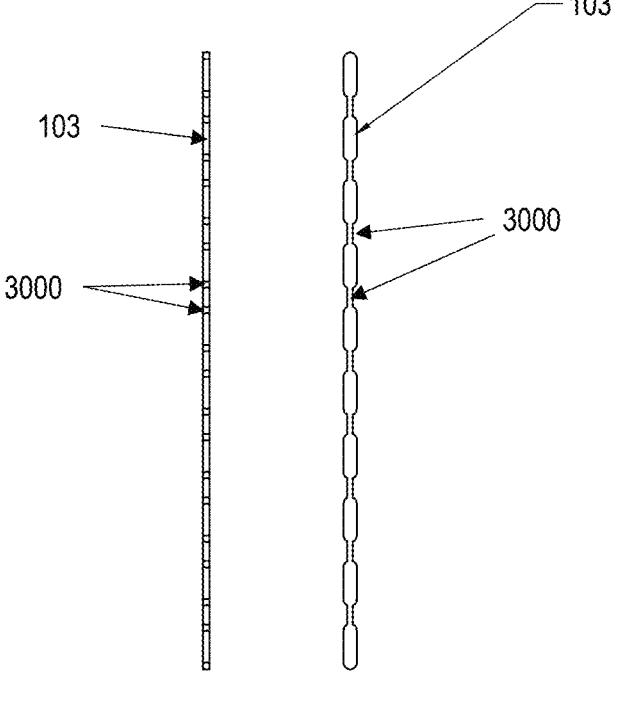
FIG. 30A illustrates another loop material according to an exemplary embodiment.
FIG. 30B illustrates another loop material according to an exemplary embodiment.

FIGS. 30A and 30B illustrate different views of an additional exemplary embodiment of the loop geometry. As shown in the portion of loop 103 illustrated in FIGS. 30A and 30B, the loop material can have indentations 3000, or grooves, along its length. The ligation loop material is formed to provide enhanced tissue gripping and enable a sliding cinch to maintain its hold on the loop.

Figure 31C:
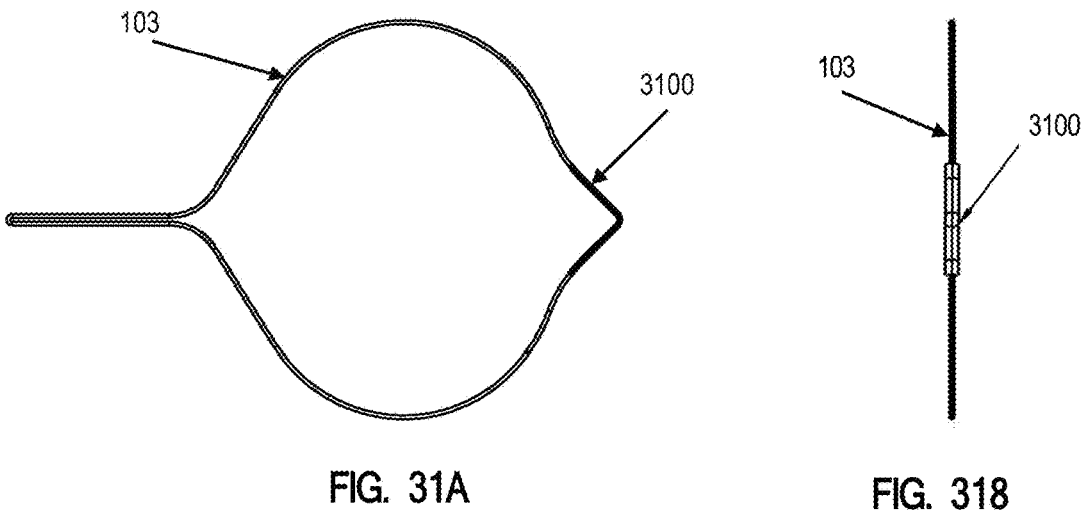
FIG. 31C illustrates a perspective view of the loop according to the embodiment illustrated in FIG. 31A.
Figure 31C:
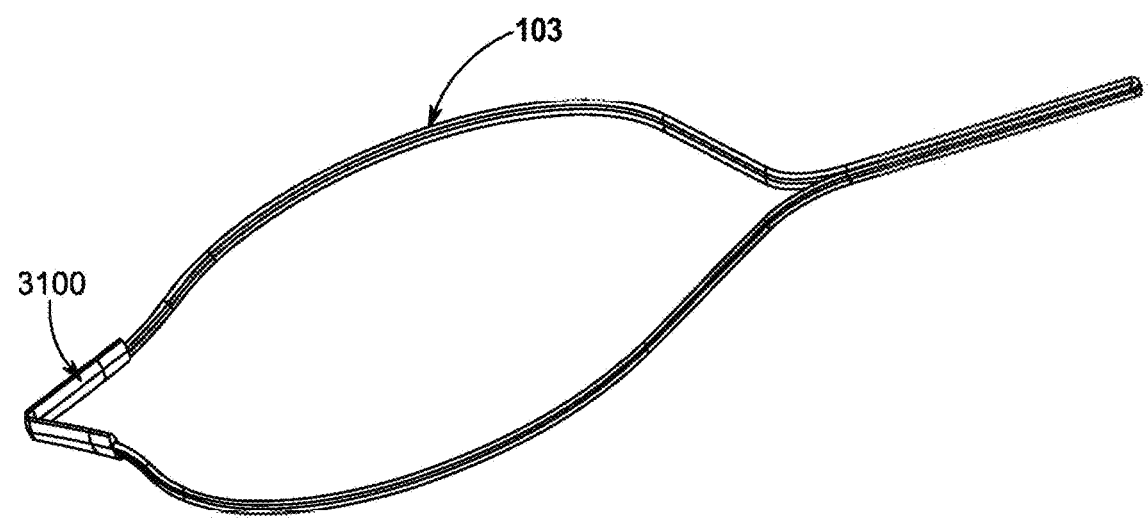

FIGS. 31A-31C illustrate another embodiment of a loop 103. The loop as shown in FIG. 31A can be made of any of the materials described herein, and can have a supplemented distal tip 3100. The distal tip of the loop can be coined, formed, or added as a separate component to the loop material at the distal end. The supplemented distal tip increases surface contact area of the loop with the tissue to be ligated. The loop 103 can be of any material, structure, and texture as described herein. FIG. 31B shows an end view of the loop illustrated in FIG. 31A. FIG. 31C shows a perspective view of the loop illustrated in FIG. 31A.

Figure 4A:
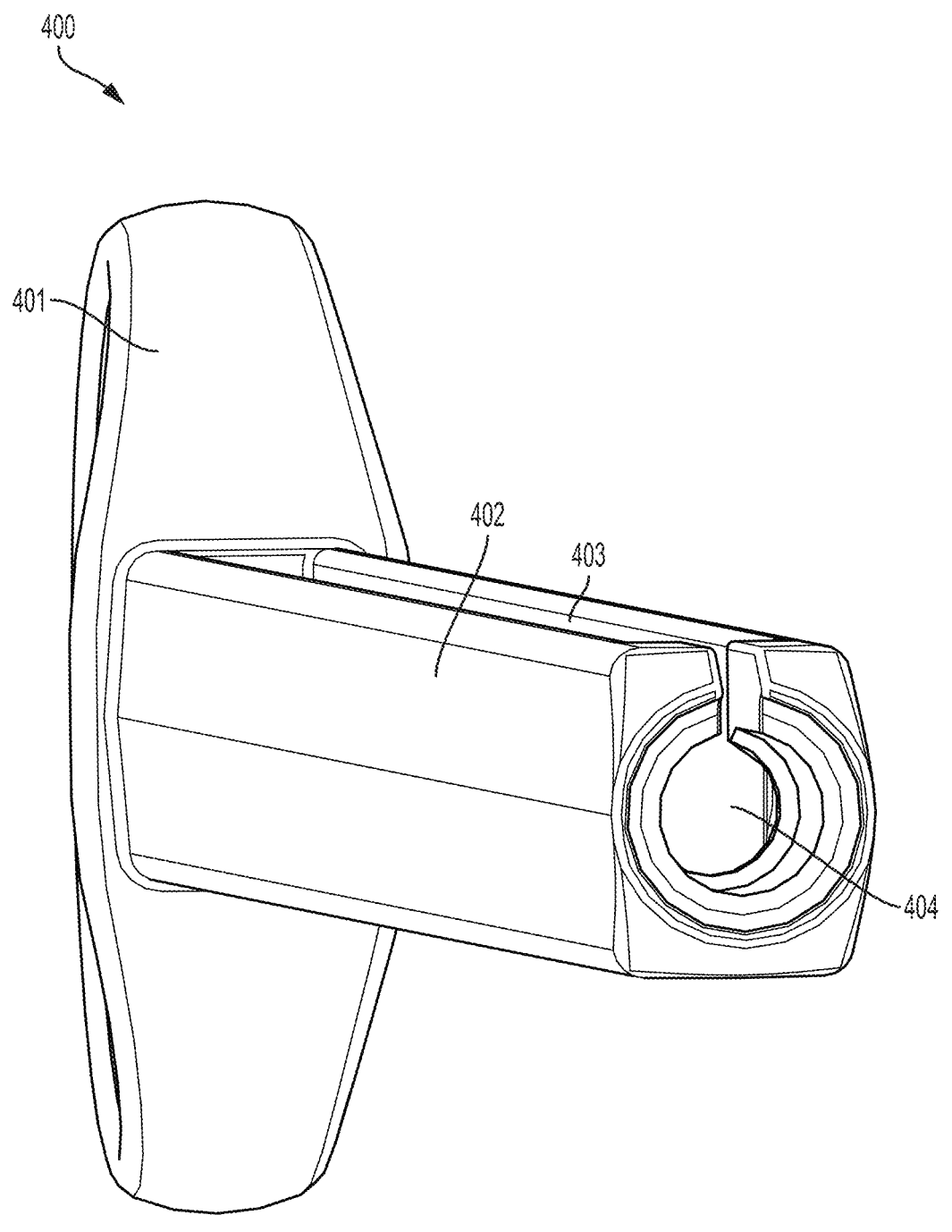
FIG. 4A depicts a handle rail in accordance with an exemplary embodiment.
Figure 4B:
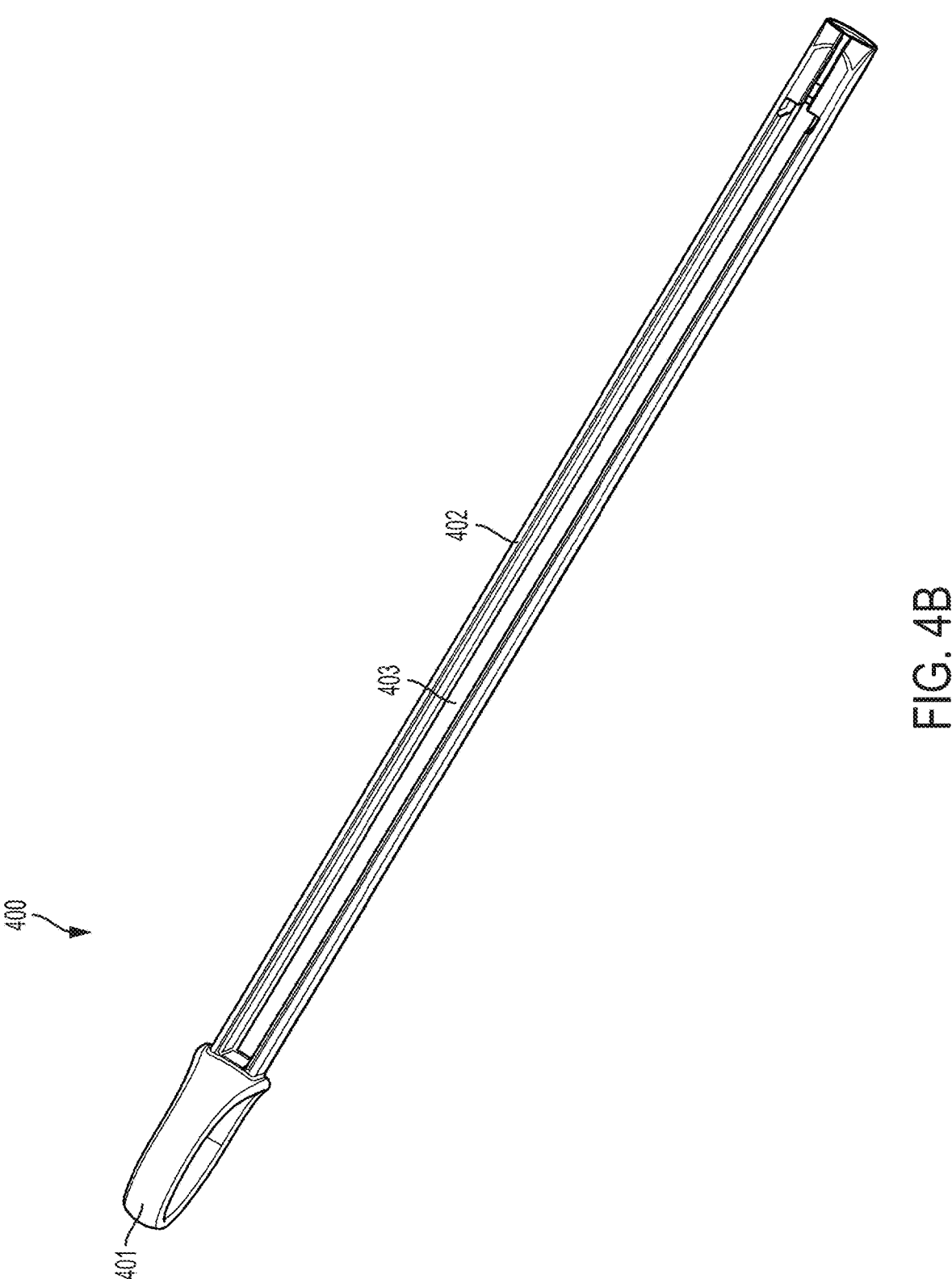
FIG. 4B depicts a top view of a handle rail in accordance with an exemplary embodiment.

FIG. 4A illustrates a perspective view of a handle rail 400, which is part of the actuator assembly at the proximal end of the ligating device 100. The handle rail has a ring 401 at the proximal end, and an elongate shaft body 402 attached to the ring, extending in a distal direction. The elongate shaft body 402 has an elongate opening 403 running along the length of the top surface of the shaft body 402. A circular opening 404 connected to the elongate opening can be at the distal end of the shaft body. FIG. 4B illustrates a top view of the handle rail 400. The opening 403 along the top of the shaft body 402 is to allow the handle 701 and spool 702 to slide in both proximal and distal directions relative to the handle rail 402. The circular opening 404 is configured to have the proximal portion 501 of the catheter sheath hub 500 fit inside the handle rail 402.

Figure 5:
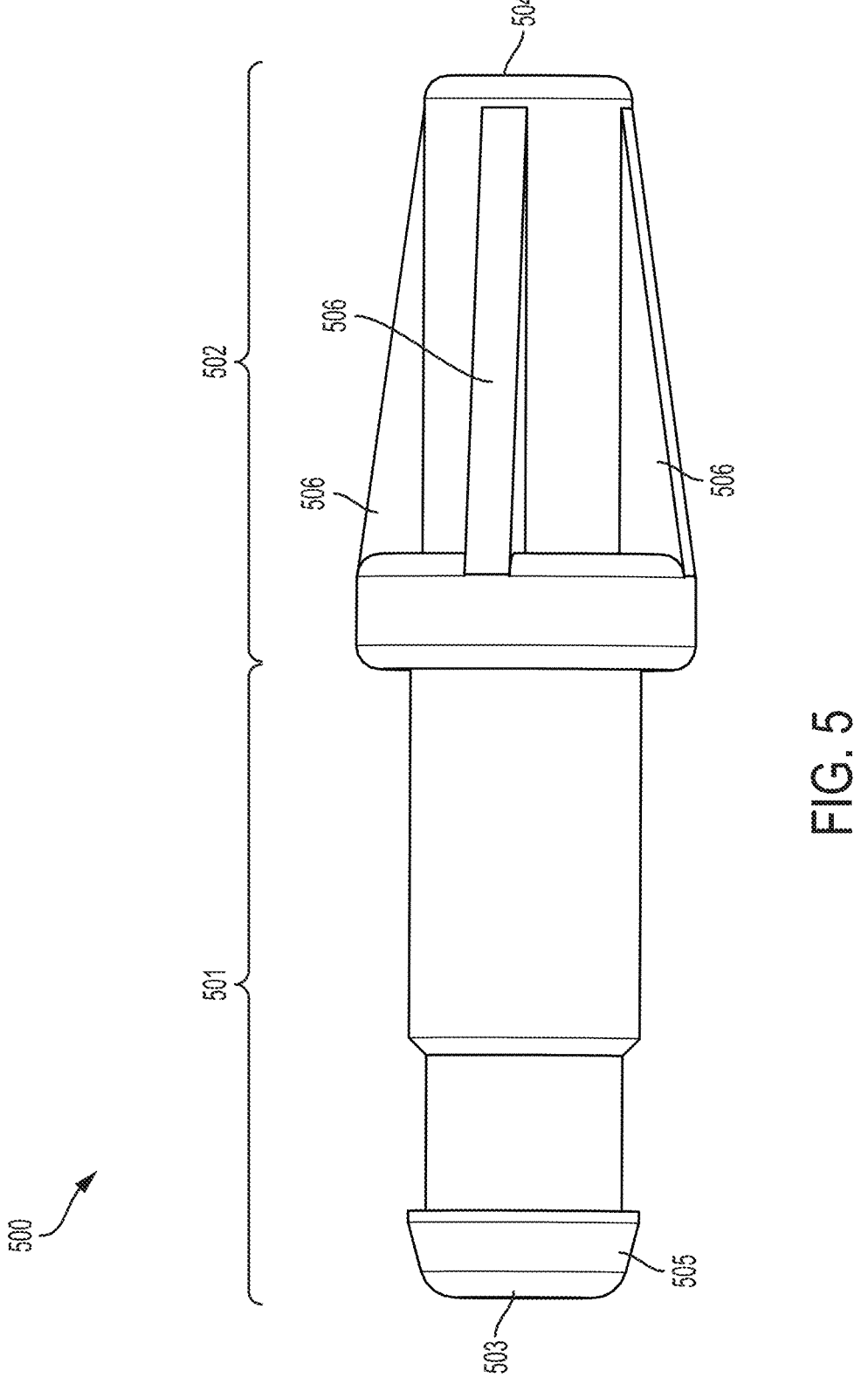
FIG. 5 depicts a catheter sheath hub in accordance with an exemplary embodiment.

FIG. 5 illustrates a catheter sheath hub 500 that can be an elongate member, and can have a proximal portion 501, a distal portion 502, and a shaft running through its longitudinal axis that is open at both the proximal end 503 and distal end 504 of the catheter sheath hub. The proximal portion 501 of the catheter sheath hub 500 can fit inside the handle rail 402. The proximal portion can be substantially cylindrical with varying diameters along its length and can have a flared portion 505 near the proximal end 503. The distal portion 502 of the catheter sheath hub 500 can have a cylindrical shape and can have fins 506 extending therefrom, where the fins are taller at a proximal location and decrease in height towards the distal end 504. The proximal end of a catheter sheath 604 fits inside the distal portion 502 through the shaft opening at the distal end 504.

Figure 6:
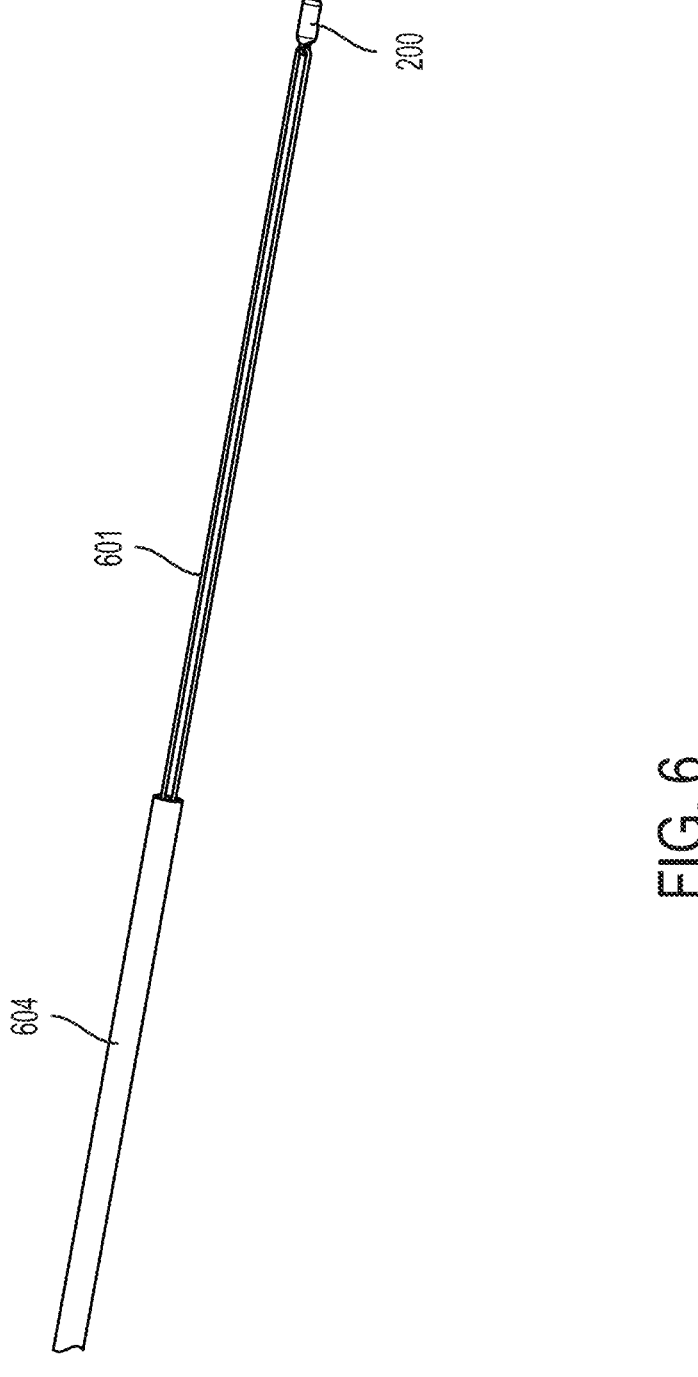
FIG. 6 depicts a distal end of a ligating device in accordance with an exemplary embodiment.

FIG. 6 is a view of the ligating assembly and the distal end of the actuator apparatus. In FIG. 6, the drive wire 601 and the hook 200 are illustrated in relation to each other. The drive wire may be solid wire filament, braided cable, hypotube, or torque cable. The drive wire, hook, and pusher (not pictured) are all sized to fit within the catheter sheath 604.

In an exemplary embodiment, the drive wire 601 extends longitudinally down a shaft of the catheter sheath in a distal direction and is threaded through the eye 201 of a hook 200, and then extends back down the shaft in a proximal direction. The drive wire can be connected at its proximal ends to a hypotube. There can be a hypotube (not illustrated) that extends from the distal end 504 of the catheter sheath hub 500, and can extend partially along the length of the catheter sheath 604, within the catheter sheath 604. The hypotube can surround a portion of the drive wire assembly, partially such that the drive wire extends from the distal end of the hypotube through the catheter sheath. The hypotube can be joined to the drive wire through crimping, swaging, or other methods known to those skilled in the art. The hypotube can serve as a connector between the drive wire to the ring handle. There can be an L-shaped bend on the proximal end of the hypotube that can be connected to the ring handle by being inserted into an opening within the ring handle or can be crimped, swaged, soldered or otherwise joined onto the handle. The distal end of the hypotube can be swaged, crimped, soldered, glued, or otherwise connected, onto a proximal end of the drive wire. The hypotube can provide additional structural support to the proximal end of the catheter sheath assembly.

In an exemplary embodiment, the drive wire can have a coating to reduce friction. For example, the drive wire can be coated with PTFE. In another exemplary embodiment, there can be a drive wire sleeve (illustrated in FIGS. 8A and 8B) surrounding the drive wire 601, which extends from the distal end 504 of the catheter sheath hub 500 through the catheter sheath 604. The drive wire can fit within a drive wire sleeve. In an exemplary embodiment having a drive wire sleeve, the drive wire sleeve can move in tandem with the drive wire. The drive wire sleeve, which can be an inner moveable sheath made of polymer, such as PEEK or PTFE, stainless steel coil or braid, or a composite of these materials as explained herein, moves separately from the hypotube. The drive wire sleeve can reduce friction that occurs when moving the drive wire. The drive wire sleeve and hypotube being moveable relative to each other can allow the drive wire to be advanced distally when in use, thus moving the cinch forward in a proximal direction. The drive wire 601, drive wire sleeve and pusher tube 602 are all contained within a catheter sheath 604. The pusher tube is connected to the spool. The pusher tube can be a polymer such as PTFE or PEEK, or PTFE-coated stainless steel, or a braided shaft encased within a polymer extrusion such that the encasement covers both sides of the outer diameter and inner diameter of the braided shaft. The pusher tube can withstand the compressional forces required to push the cinch. In addition, the catheter can include an internal additive to increase lubricity or can include a surface treatment or coating, such as PTFE to reduce friction. The pusher tube can also have any of these coatings and/or features and can also have an engineered surface, such as a grooved or ridged surface. This can help to reduce any increase in friction between the peak and the inner diameter of the catheter sheath, caused by having a peak that is more stiff than the coil.

Figure 7A:
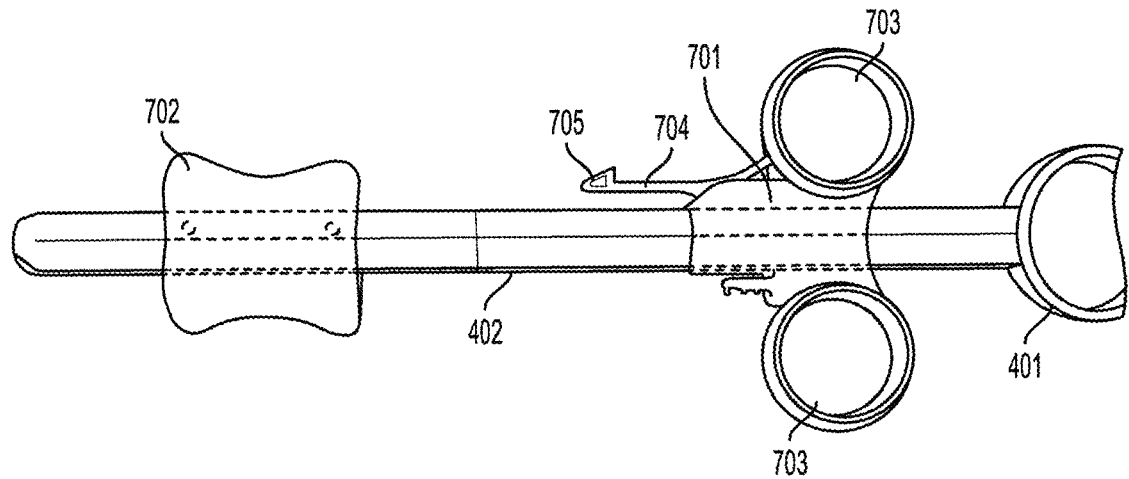
FIG. 7A depicts a proximal end of handle assembly in accordance with an exemplary embodiment.

FIG. 7A illustrates a closer view of components at the proximal end of the actuator apparatus 100. The handle rail 402 with proximal ring 401 is visible. The distal end of the handle rail 402 is configured to attach to the proximal portion of the catheter sheath hub 500. A ring handle 701 is slidably attached to the handle rail 402, and can have two ring-shaped finger openings 703. A spool 702 as described herein is also slidably attached to the handle rail 402. The ring and spool can be removably connected to each other, and can be connected to each other in a manner to prevent premature separation. In an exemplary embodiment, the ring handle 701 can have a prong 704 with a lip 705 on it. The lip 705 can latch onto the spool, thereby connecting the ring handle with the spool. The ring and spool can be removably attached to each other via other mechanisms (not shown), as well. In an exemplary embodiment, the spool and ring handle can have male and female components, and can be removably connected to each other through a slight interference fit between the male and female components. In another exemplary embodiment, one of the spool or ring handle can have male threads and the other can have female threads. Instead of male/female threads, a lip/groove feature can be on the spool and ring handle components. In the threaded and lip/groove embodiments, the threads or lip and groove could be required to be irreversibly broken by the application of a threshold force to separate the ring handle and the spool, thus preventing accidental deployment without application of the threshold force. This threshold force can be in the range of 1 to 45 Newtons or ¼ to 10 lbs of force, and more specifically can be in the range of force likely to be applied by a user, such as ¼ lb to 2 lbs, and even more specifically from ¼ pound to 1 pound. In another exemplary embodiment, the spool and ring handle can be connected via a peel-away strip (not shown). The ring handle and the spool can be anchored together with a peel away strip so that the two parts can be separated, but only after pulling this strip, to ensure it does not occur prematurely. Features described in exemplary embodiments herein can be used to reconnect the ring handle and spool.

Figure 7B:
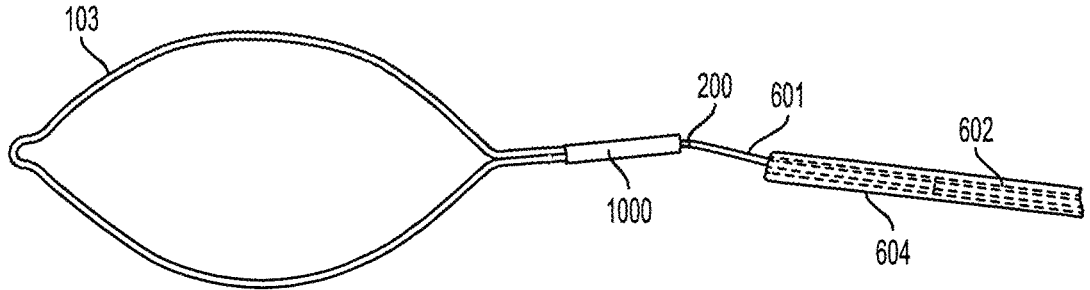
FIG. 7B depicts a distal end of a handle assembly in accordance with an exemplary embodiment.

Referring to FIG. 7B, another view of the distal end of the ligating device 100 is illustrated. There is a catheter sheath 604 with a pusher 602, which can be a pusher tube, inside of it, and a drive wire 601 attached to the distal end of the pusher tube 602. The drive wire is attached to an eye 201 at a proximal end of the hook 200 and a loop 103 can be removably positioned on the distal end 204 of the hook 200. The drive wire can be attached to the hook by being threaded through an eye in the hook, crimping, soldering, brazing, or other means known to those skilled in the art.

A cinch component 1000 is used to tighten the loop 103, and once the loop is in a proper position, to ligate tissue. The cinch component can be a tubular cinch geometry and can have a proximal region 1001 and a distal region 1002. The distal region is the portion that cinches the ligating element once it has been positioned around tissue of interest. The proximal region is the portion that maintains the engagement between the hook 200 and the proximal end of the ligating element 103 until the ligating element has been cinched and is ready to be left on the tissue of interest. The proximal region can have different material properties than the distal region. For example, the distal region can be made of a stronger material or larger cross section to increase its stiffness. The distal region may be composed of a polymer that swells, shrinks, changes shape and/or loses strength in the presence of an aqueous environment or elevated temperature, such as that found within the body. The proximal region may be made thinner than the distal region to promote ease of attachment to hook 200. The proximal region may also be crimped, tapered, bent or otherwise modified to promote retention of the hook within it. The loop can be made of a composite polymer with variable durometer or stiffness along its length to achieve the same effect without changing the loop cross section. The loop size and bend radii may also be modified to promote stiffness by, for example, decreasing the loop size. Alternatively, a uniform cross section and material may be used for the loop and modifications can be made to the material or structure of the cinch 1002 to promote stiffness of the loop. For example, the cinch can have constraining individualized lumens to help keep the loop in plane under load (not illustrated). The individualized lumens can travel along with or separately from one another along the longitudinal direction of the cinch component. One strand of the loop can run through each of the individualized lumens instead of two strands of the loop running through a central lumen in the cinch component. Also, the cinch length can be increased to hold a greater part of the loop within it. The cinch can be made of a polymer such as polytetrafluoroethylene (PTFE), polyether ether ketone, or other heat shrink polymer or of electrically nonconductive or non-magnetic material. The proximal region and distal region can be made of the same material, or different materials, or can be made on a gradient such that the properties of the proximal end and distal end are different, changing gradually along the length of the cinch. Further, either the distal or proximal region can also be made of a stronger material, such as ceramic or metal, with features to provide the cinching and retaining function of the cinch component.

A clip 1801 having a loop at its proximal end can also be removably positioned on the distal end 204 of the hook 200. In the clip embodiment, the cinch component 1000 is used to close the clip around tissue.

The distal end of the pusher tube is in contact with the proximal end of the cinch component, which when being positioned is also connected to the ligating element and the hook at the distal end of the drive wire. In this position, the hook and proximal end of the loop are within the cinch component, and both the hook and the ligating element (loop) are retained in place by a friction fit. The hook is removably connected to the loop. When the pusher tube and drive wire are moved in a distal direction together there is no relative movement between the cinch component and the hook holding the proximal end of the loop, thereby allowing all the components within the catheter sheath to move without causing irreversible cinching or deployment of the ligating element. The ligating element can be repositioned or withdrawn back in the delivery catheter by moving the drive wire and pusher tube together in a proximal direction. The proximal portion of the cinch component 1000 holds the hook in place on the proximal end of the ligating element.

FIG. 8A illustrates a closer view of the arrangement of the elongate members of the ligating device 100 at their distal ends. Catheter sheath 604 houses a pusher tube 602 and a drive wire 601. The pusher tube 602 can be a coil. The coil can be a spring coil. The coil can be made of stainless steel, ceramic, or other material having suitable columnar strength and/or stiffness to be used to push the cinch forward in a distal direction and flexibility to adapt to twists and during use in the catheter sheath. In another exemplary embodiment, the pusher tube can be reinforced with a braided mesh, or can be a braided shaft. In another exemplary embodiment, the pusher tube can be a Nitinol tube or a laser-cut hypo tube. The reinforced shaft surrounds the drive wire sleeve 603, which houses the drive wire 601. In an alternative embodiment, the pusher tube can be a tube with holes cut into it to add flexibility, through a technique such as laser cutting or electrical discharge manufacturing. In an exemplary embodiment, the catheter sheath can also house an optional drive wire sleeve 603. The drive wire sleeve 603 can help reduce friction. Alternatively the pusher tube 602 can be coated or have an engineered surface, e.g. ridged or grooved surface, to reduce friction. The catheter sheath can also have an additive or be coated to reduce friction. The drive wire 601 extends out past a distal end of the drive wire sleeve 603, which surrounds the drive wire, and past a spring coil, and past the distal end of the catheter sheath 604. The drive wire 601 is threaded through the eye 201 of the hook 200. The pusher tube and extends from the distal end of the catheter sheath hub to the distal region of the catheter sheath.

FIG. 8B illustrates a cross section view of the catheter sheath and all the components that fit within it. In this view, the outermost circle is the catheter sheath 604. Within the catheter sheath 604 is a pusher tube 602. FIG. 8C illustrates a cross-section view taken along line C-C in FIG. 8B.

Figure 9A:
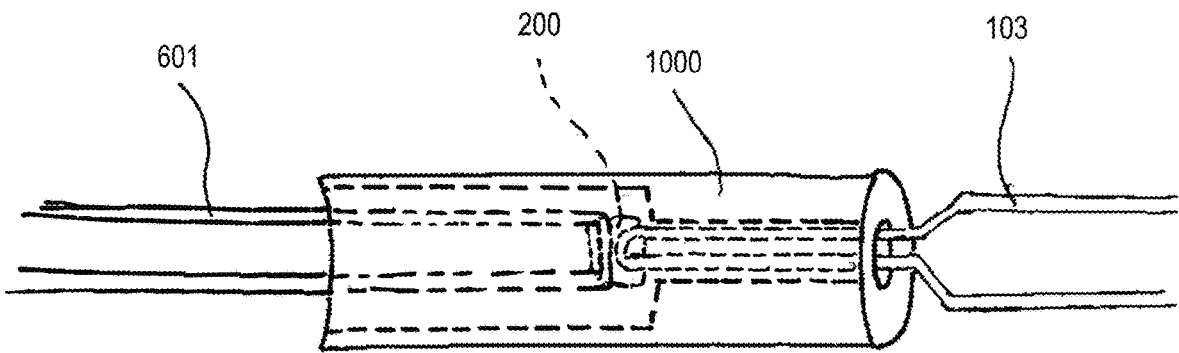
FIG. 9A depicts a close-up view of the cinch and hook assembly and catheter sheath in accordance with an exemplary embodiment.
Figure 9B:
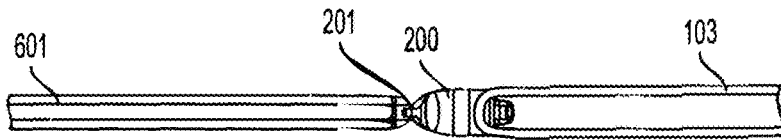
FIG. 9B depicts a close-up view of the cinch and hook assembly of FIG. 9A with the cinch component removed.

FIG. 9A illustrates a close-up view of the cinch and the hook and how they fit within a catheter sheath. FIG. 9B illustrates the same components but with the catheter sheath removed, thus illustrating the interconnectivity of the cinch and hook. In FIGS. 9A and 9B, the drive wire 601 is threaded through the eye 201 of the hook 200. The proximal end of the loop (or clip, not illustrated) is removably positioned on the distal end 204 of the hook 200.

The cinch component 1000 (FIG. 10C) can be made as a molded component, or through an extruded tubing bonded process, or made with the same techniques used to make a rapid prototype part. The cinch component can have a bore running through it along a longitudinal axis. The bore can be a constant diameter throughout the length of the cinch component or it can vary and be smaller at one end than the other end of the cinch component 1000, to provide a cinching function and hook retaining function, respectively. The interior of the cinch component 1000 can be shaped to guide the loop and have a portion small enough to cinch the loop when in use. The drive wire 601 and the hook 200 with the loop 103 around the distal end 204 of the hook can be positioned within a proximal portion of the cinch. a distal end of the cinch can have a size configured to slide over and cinch tight the ligating element when the assembly is in use. The loop is pulled back into the inside of the cinch component, and then is pulled further back as the cinch is activated and moved in a distal direction relative to the loop.

In an exemplary embodiment of a cinch component that is constructed as a single component, both retaining and cinching features can be built into a single component. The retaining portion may be of substantial inner dimension to allow for connection of the hook to a loop such that they will not disengage from one another. The inner diameter can be tight enough to retain the hook on the loop. The cinch component can include features to promote retention of the hook beyond the sizing of the inner diameter of the retaining portion. Such features can include, but are not limited to, a taper, crimp, bend, joint, or bent in tabs that would not permit the hook from being removed from the cinch without a threshold force being applied to it. This force could be of similar or lesser magnitude to that needed to dislodge the handle components from one another without engaging the release button.

The cinch component can be made through injection molding, 3D printing, or other known means in the art. The cinch component can have cutouts in it to provide additional softness and/or flexibility. The cinch component can be made of ceramic, PEEK, PTFE, or other known materials.

Figure 10A:
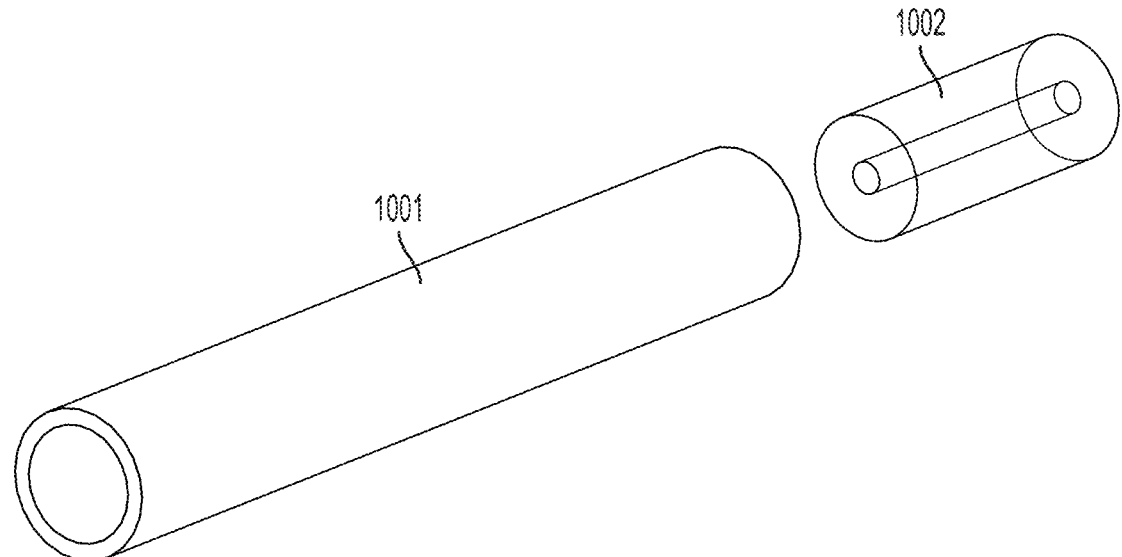
FIGS. 10A and 10B depict a two-piece cinch component in accordance with an exemplary embodiment.
Figure 10B:
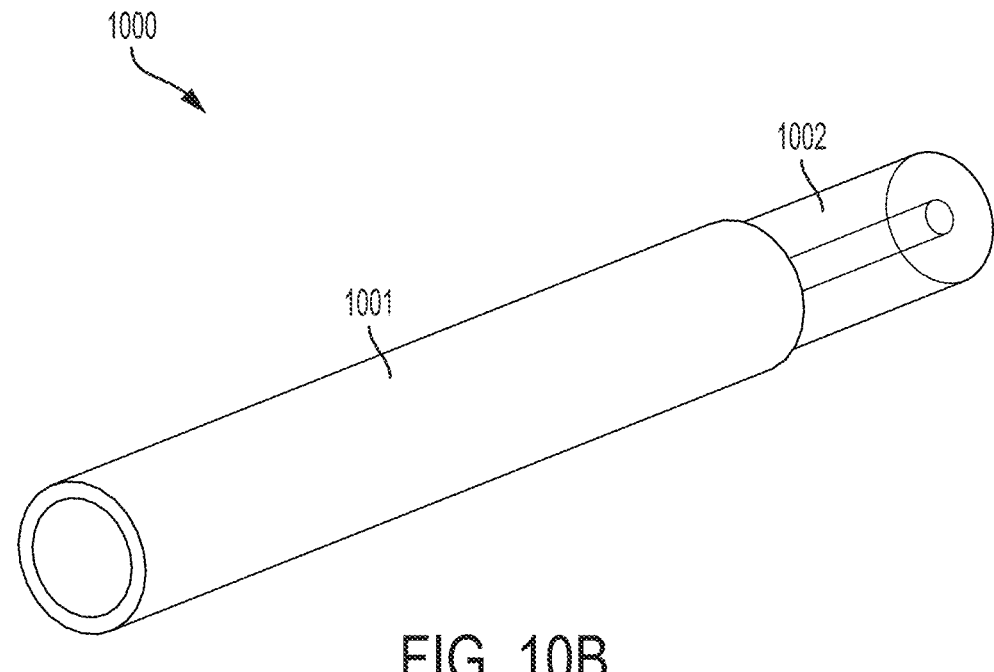
Figure 10C:
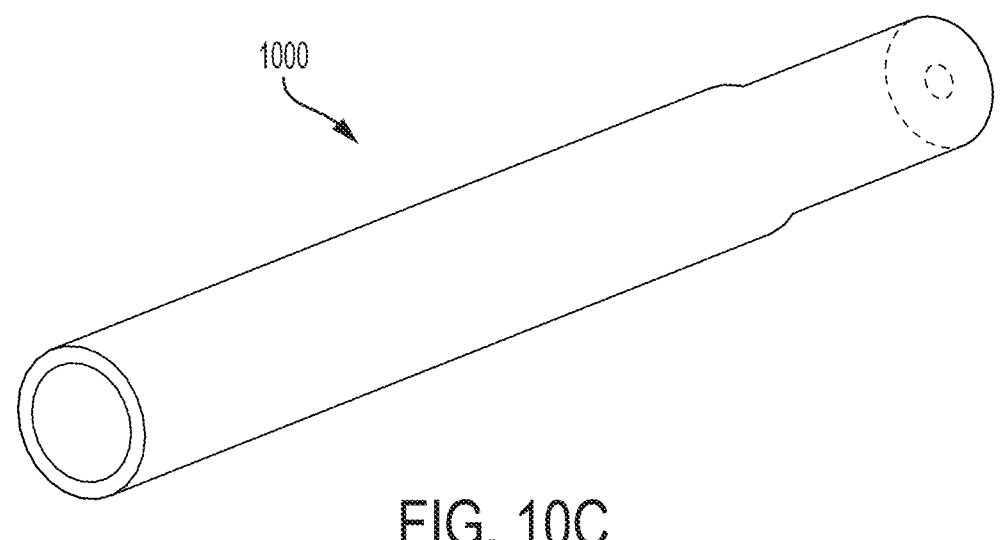
FIG. 10C depicts a one-piece cinch component in accordance with an exemplary embodiment.

The cinch component 1000 can be made of a single component, as shown in FIG. 10C or can be made as multiple components. The cinch component 1000 (FIG. 10A) can be made of two components, illustrated as separate components in FIG. 10A, and illustrated together as a cinch component 1000 in FIG. 10B. The distal cinch component 1002 can be cylindrical in shape and can have a bore running through it along a longitudinal axis. The cinch may contain a single lumen or a plurality of lumens. The proximal cinch component 1001 can be a cylindrical shaped shell, open at both proximal and distal ends. The proximal cinch component 1001 can be made of polyether ether ketone (PEEK) or other polymers or of electrically nonconductive or non-magnetic material. The distal cinch component 1002 can be made of a heat-shrink polymer such as polytetrafluoroethylene (PTFE). As explained above, using a material like PEEK or PTFE can reduce friction.

Figure 11A:
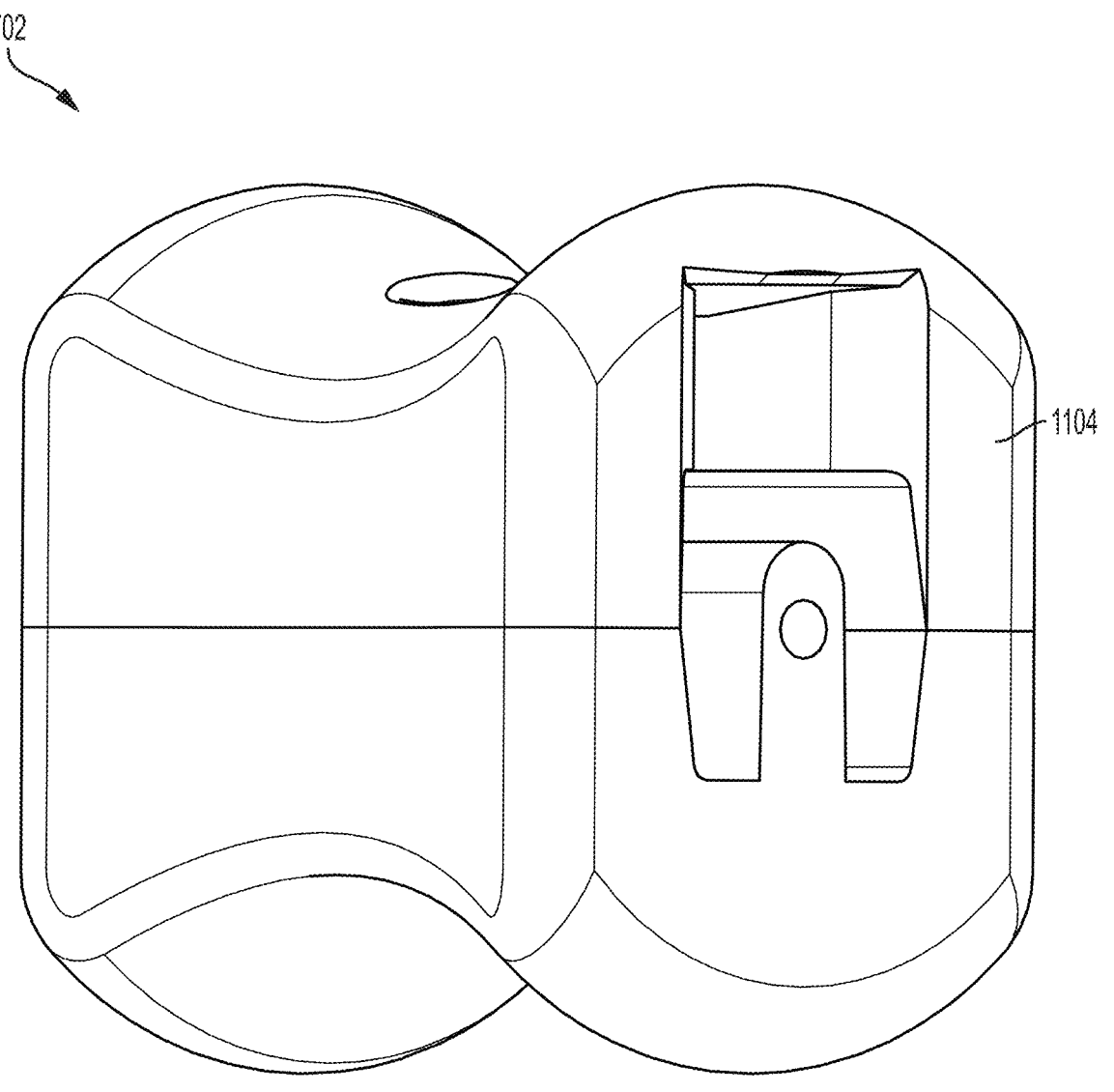
FIG. 11A depicts a perspective view of the proximal end of a spool in accordance with an exemplary embodiment.
Figure 11B:
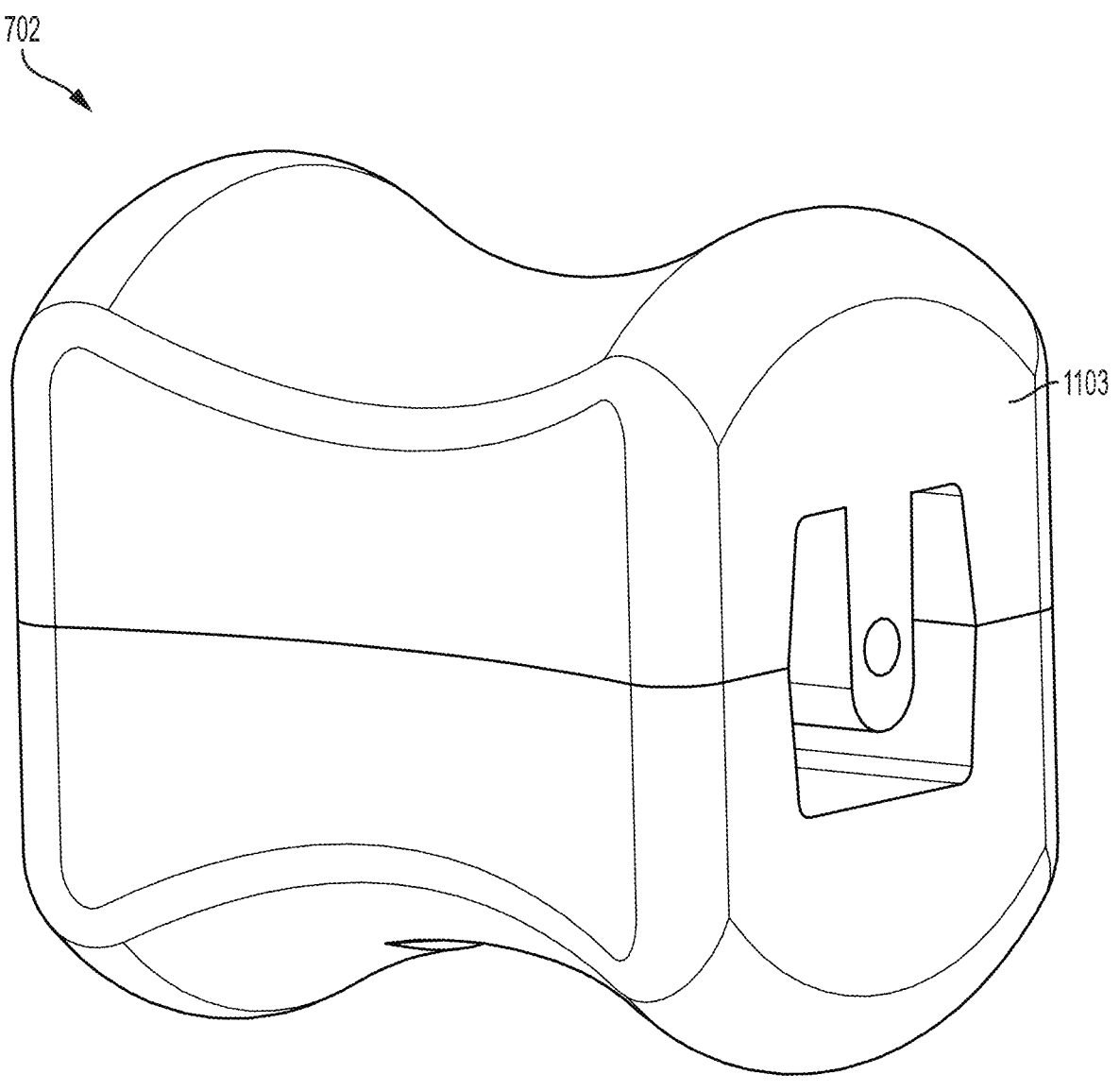
FIG. 11B depicts a perspective view of the distal end of a spool in accordance with an exemplary embodiment.
Figure 11C:
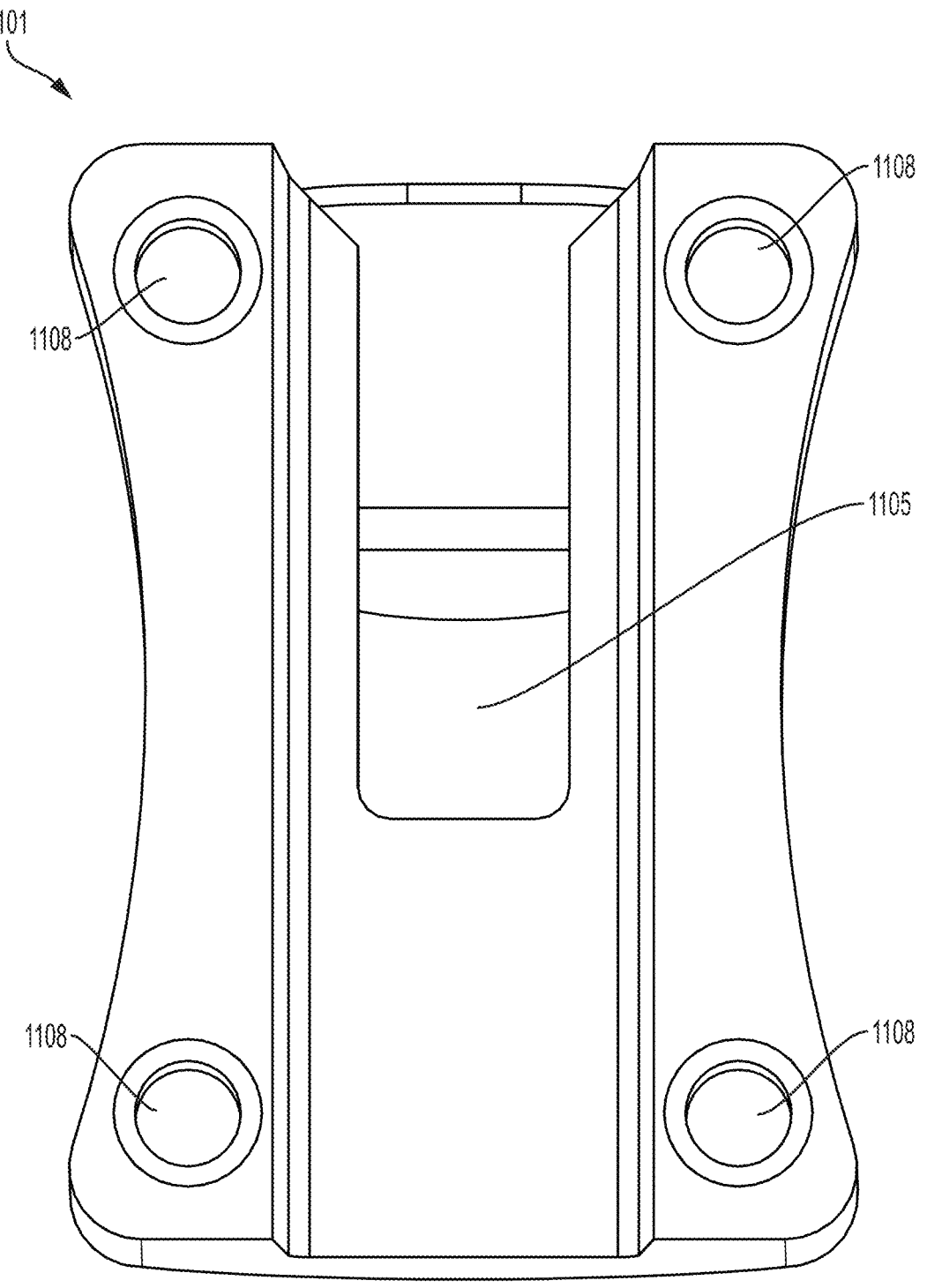
FIG. 11C depicts a bottom view of a top piece of a spool in accordance with an exemplary embodiment.

FIG. 11A illustrates a sliding element 702, which is a type of handle, which can be a spool, that is positioned around the handle rail 402. The spool 702 can be made of a polymer. The spool is referred to as such due to its spool-like shape, but is not limited to such shape. It can be any shape that the device user of the device, such as a nurse, can effectively actuate. The spool can be cylindrical, spherical, or box-like in shape, for example. The spool can have curves and/or corrugations on its outer surface. The spool 702 can be made of two components, the upper half 1101 and the lower half 1102. The spool 702 has a distal end 1103 and a proximal end 1104. The spool has an opening running therethrough to allow the spool to be slidably fit on the handle rail. The proximal end as seen in FIG. 11A has an opening configured to fit the handle rail 402 and also to fit the prong 704 of the ring handle when the loop 103 is adapted to acquire tissue or release the tissue after being cinched. The distal end 1103, as seen in FIG. 11B, has an opening configured to fit the handle rail and allow the spool to slide along the handle rail. The distal end opening is a size and shape that matches the cross-section area of the handle rail 402. The proximal end opening can be differently shaped than the distal end opening to accommodate the prong of the ring handle, when it is connected to the spool. The upper half of the spool 702 has an opening 1105 at the top that extends through the top piece 1101 into the center of the spool where the handle rail 402 extends through, as illustrated in FIG. 11C. The top opening 1105 is configured to allow the prong 705 of the distal end of the ring handle to pass through and catch on the spool so that the spool 702 and the ring handle 701 become fixedly connected to each other. The prong 705 may be designed to mate to the spool 702 using alternative shapes and connection schemes such as, for example, tabs and slots, threads, ball and socket joints, grooves, pins, latches, flanges and other methods apparent to those skilled in the art.

Figure 11D:
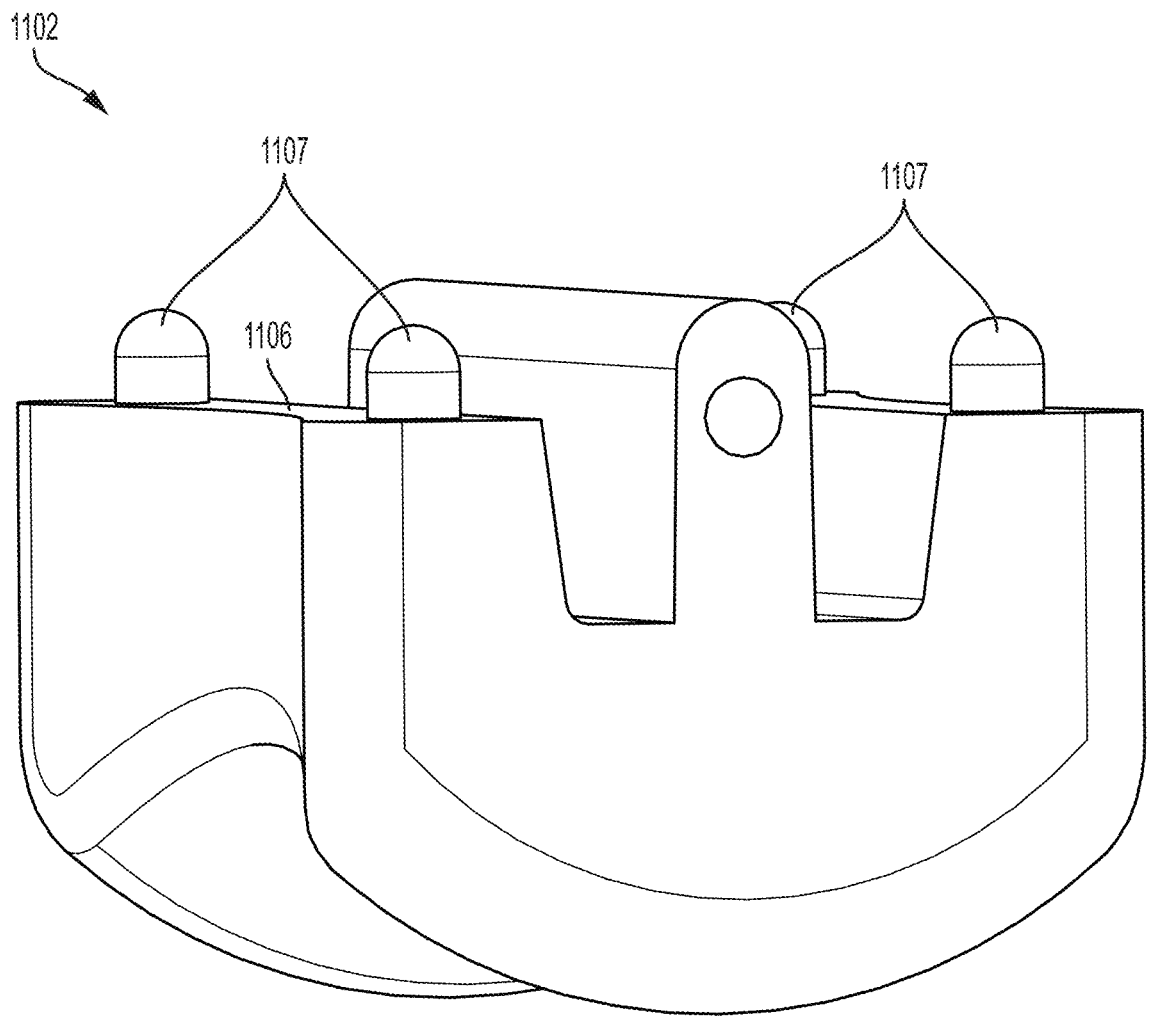
FIG. 11D depicts a distal perspective view of a bottom half of a spool in accordance with an exemplary embodiment.

FIG. 11C illustrates a bottom view of the top piece 1101 of the spool 702. Here, the top opening 1105 for the prong 705 of the rail handle 701 is visible. As an exemplary embodiment, FIG. 11C illustrates the detail of the bottom view and an example of how it can be shaped to catch the prong 705. There can also be openings 1108 that extend into the bottom surface of the top piece, configured to fit the posts 1107 extending from the top of the bottom piece 1102 of the spool, as illustrated in FIG. 11D. FIG. 11D illustrates the bottom piece of the spool 1102. The upper surface 1106 of the bottom piece in this embodiment has four posts 1107 extending therefrom, configured to fit into corresponding openings in the top piece. This is one way that the pieces of the spool can be fit together, however, other means of attachment can also be used. In another embodiment, the spool can be molded from one piece of polymer.

The components as described above are designed to work together as a ligating device, to ligate and block blood flow to tissue, such as that from polyps or other tissue that could be cancerous or otherwise abnormal. In use, the loop 103 is extended from the catheter sheath 604 and placed around the tissue to be removed, for example, a polyp. However, the assembly is not limited to this use.

Figure 12A:
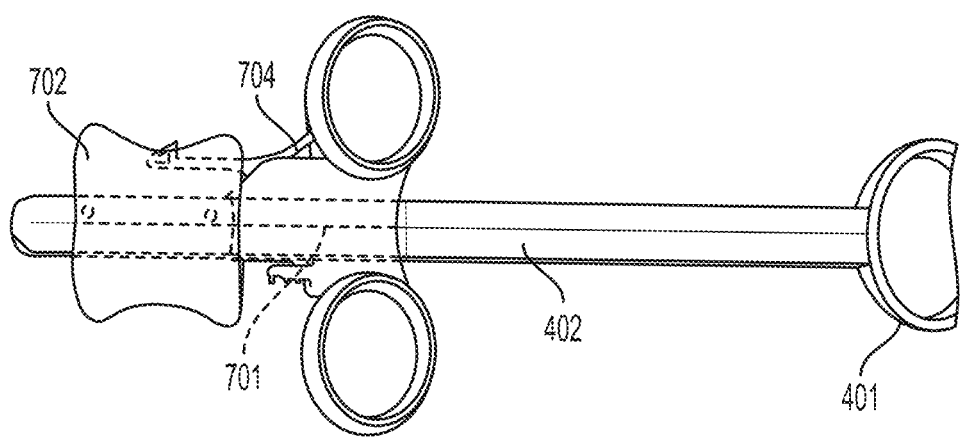
FIG. 12A depicts a handle at the proximal end of a ligating device in a first position.

FIGS. 12A-17B illustrate the use of the device and how the components are fit together, when a loop is used at the distal end of the device. FIGS. 12A and 12B illustrates the loop 103 extended from catheter sheath 604 and the relative positioning of the actuator assembly components at the proximal end. FIG. 12A illustrates the proximal end of the ligating device 100. In FIG. 12A, the ring handle 701 and the spool 702 are connected to each other, and are spaced apart from the proximal ring 401. The movement of the spool 702 and ring handle 701 (together) in a distal direction causes the loop 103 in FIG. 12B to be extended from the catheter sheath 604. In FIG. 12B, the loop 103 is extended distally from the catheter sheath 604. This distal movement opens the loop 103 so that it can be positioned around tissue 1201 as illustrated in FIG. 12B. Moving the spool and ring handle in a proximal direction along the handle rail 402 retracts the loop 103 back within the catheter sheath 604. The spool 702 and ring handle 701, when they are connected, as illustrated in FIG. 12A, can be moved proximally and distally as many times as the user desires to adjust the amount of the loop extended from the distal end of the catheter sheath, to assist with positioning the loop.

Figure 12B:
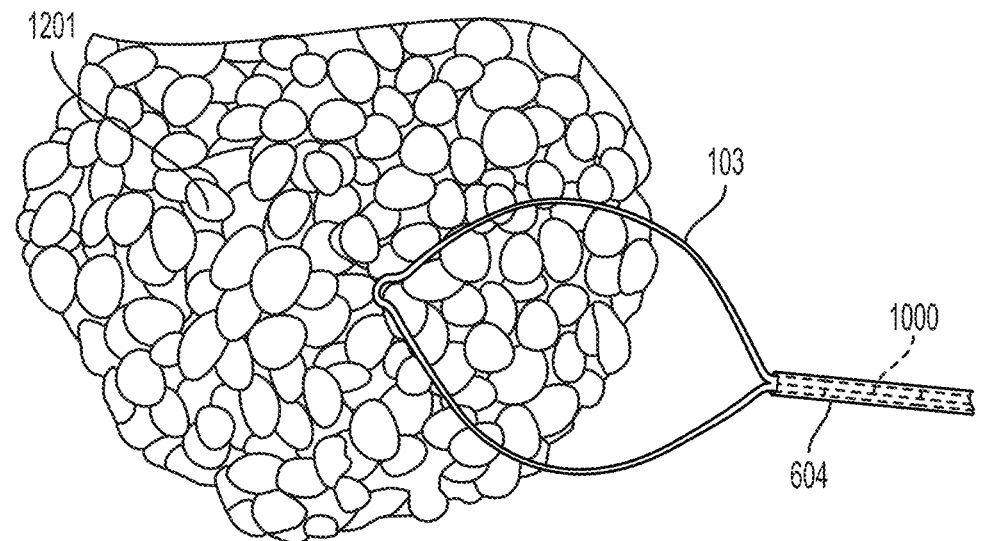
FIG. 12B depicts a loop extended from a distal end of a catheter sheath in a position corresponding to the position of the device in FIG. 12A.
Figure 13A:
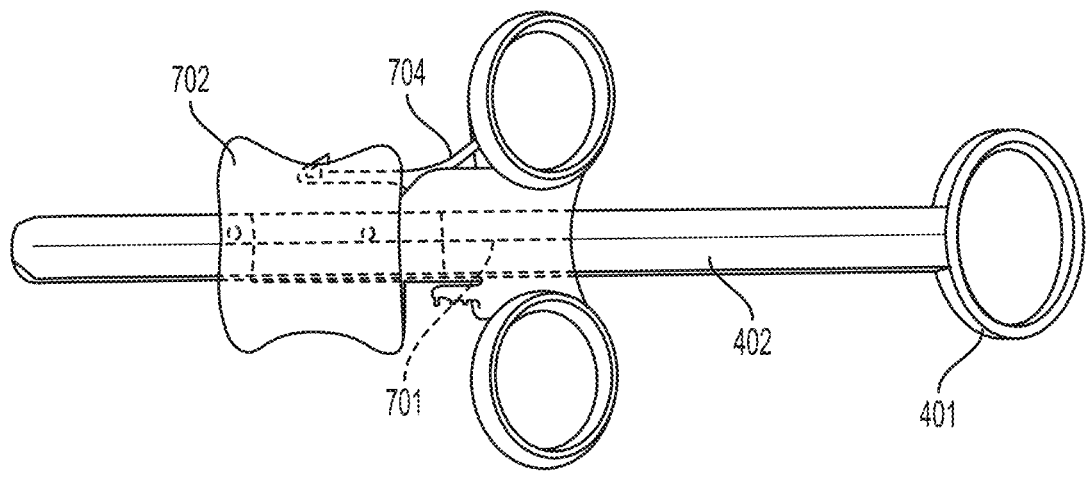
FIG. 13A depicts a handle at the proximal end of a ligating device in a second position.
Figure 13B:
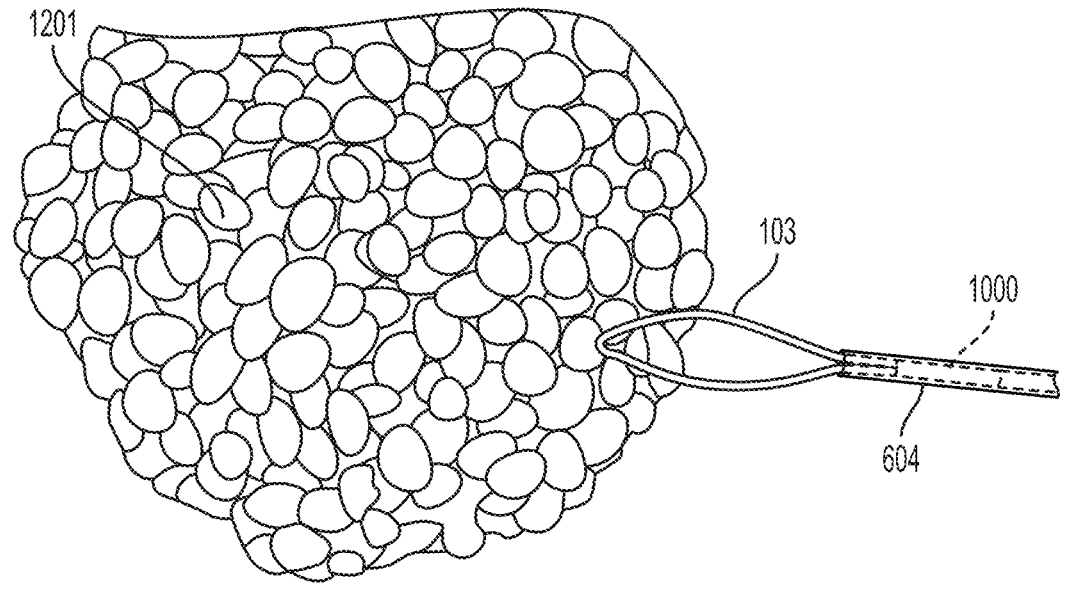
FIG. 13B depicts a loop extended from a distal end of a catheter sheath in a position corresponding to the position of the device in FIG. 13A.

FIGS. 13A and 13B illustrate the proximal and distal ends, respectively, of the ligating device 100 when the spool and ring handle are more proximally located on the handle rail than in FIGS. 12A and 12B. FIG. 13A illustrates the spool 702 connected to the ring handle 701 and positioned closer to the proximal ring 401 than is illustrated in FIG. 12A. FIG. 13B shows the corresponding loop, with the opening of the loop smaller than in FIG. 12B because the loop has been at least partially retracted back within the catheter sheath.

Figure 14A:
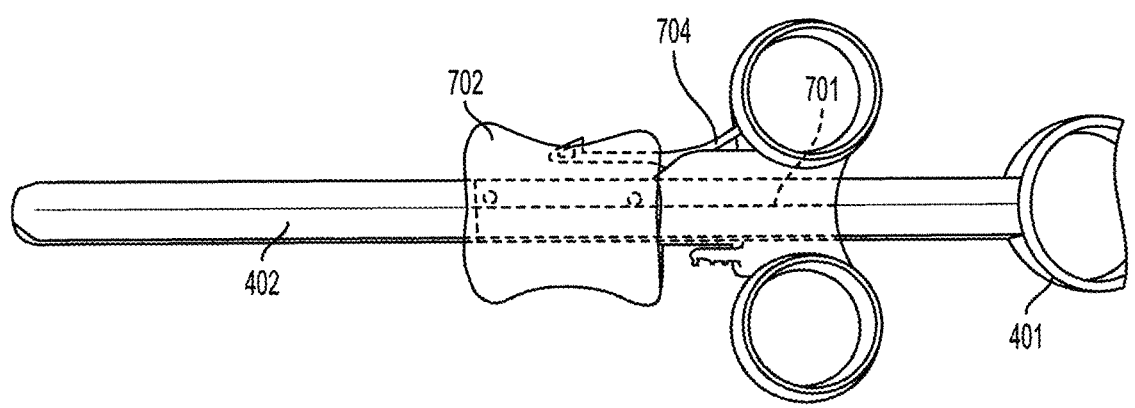
FIG. 14A depicts a handle at the proximal end of a ligating device in a third position.
Figure 14B:
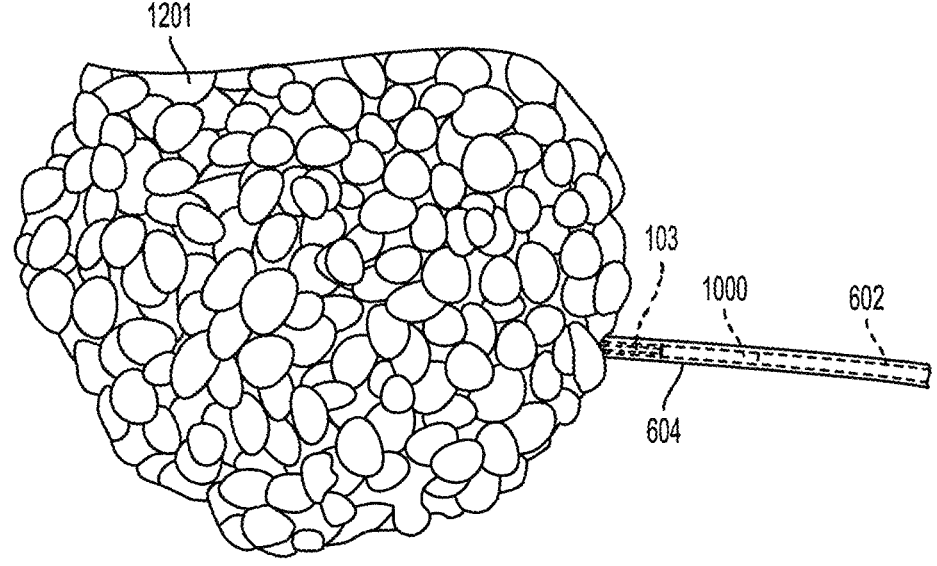
FIG. 14B depicts a loop extended from a distal end of a catheter sheath in a position corresponding to the position of the device in FIG. 14A.

FIGS. 14A and 14B illustrate the ligating device 100 when the spool and ring handle are moved even farther in a proximal direction, toward the ring handle 701. FIG. 14A, illustrates the proximal end of the ligating device 100, and illustrates that the spool 702 and ring handle 701 are still together. FIG. 14B illustrates the position of the loop 103 that corresponds to the spool and ring handle position. In FIG. 14B, the loop has been tightened around the tissue 1201 to be ligated. More of the loop is contained within the catheter sheath assembly than in FIG. 13B as a result. The spool and ring handle can be moved in a proximal direction until the loop 103 is brought to its desired tightness, where the tightness can be increased by withdrawing more of the loop back into the catheter sheath. A desired tightness can be one that restricts blood flow to the tissue surrounded by the loop. The proximal movement of the spool pulls the pusher tube in a proximal direction, and the proximal movement of the ring handle pulls the drive wire, hook, cinch and ligating element in a proximal direction in equal proportion to that of the pusher tube. That is, the assembly of the spool and ring handle, pusher tube, drive wire, hook, cinch component, and ligating element do not move relative to each other, but relative to the handle rail and catheter sheath. The hook does not release the loop when the cinch component is covering the hook.

Figure 15A:
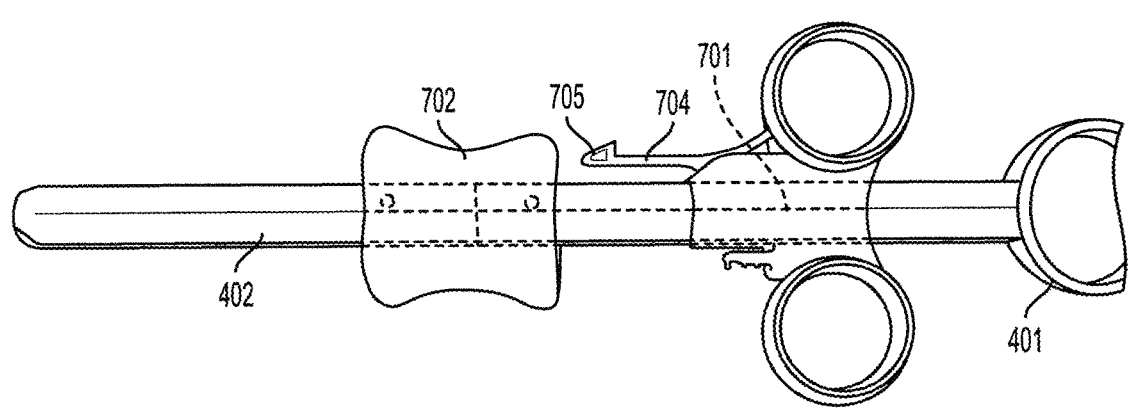
FIG. 15A depicts a handle at the proximal end of a ligating device in a fourth position.
Figure 15B:
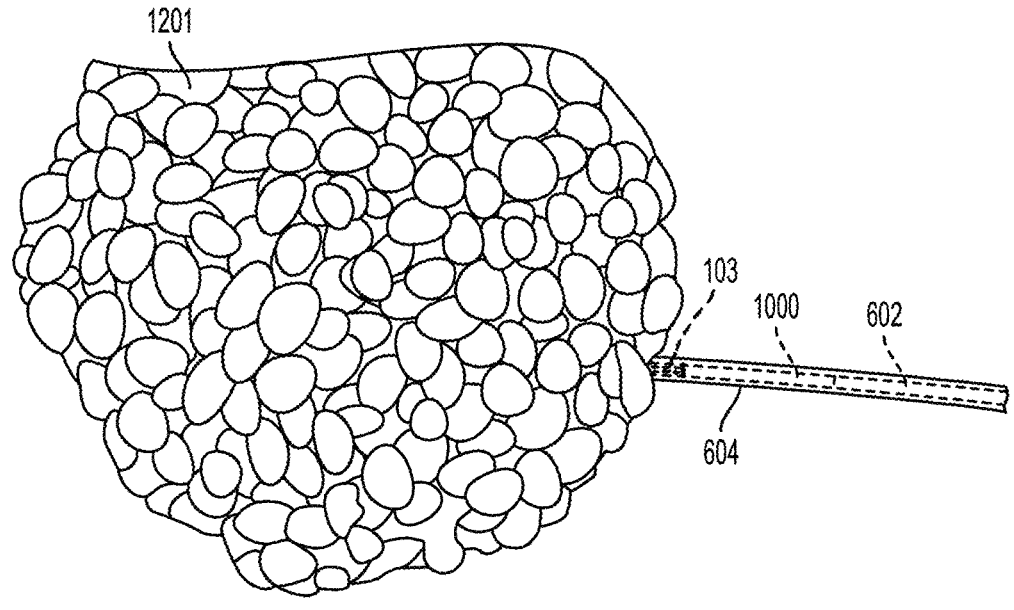
FIG. 15B depicts a loop extended from a distal end of a catheter sheath in a position corresponding to the position of the device in FIG. 15A.

FIGS. 15A and 15B illustrates the proximal and distal ends, respectively, of the ligating device 100 when the cinch component 1000 starts to become engaged. The ring handle can become disengaged from the spool, as illustrated in FIG. 15A. In an exemplary embodiment, the ring handle can become disengaged from the spool when the protrusion 705 on the distal end of the ring handle prong 704, which is accessible through the opening 1105 at the top of the spool 702 is depressed by the user. Depressing the protrusion, which can also be referred to as a lip or a button, allows the user to separate the spool from the ring handle. The user moves the spool in a distal direction along the handle rail 402. This movement of the spool causes the pusher element 602 to move in a distal direction and thereby push the entire cinch component distally down over the ligating loop, while the lack of movement by the handle 701 maintains the current position of the drive wire and hook at the distal end of the drive wire. Engagement of the cinch with the loop is what locks the loop in place. FIG. 15B illustrates the loop 103 around tissue 1201 when the spool and ring handle are separated from each other and the cinch component is beginning to be engaged.

Figure 16A:
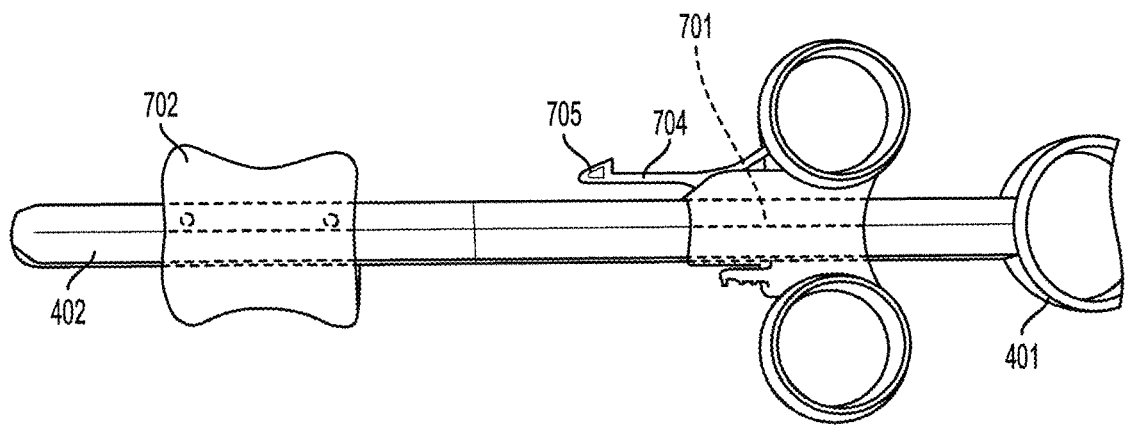
FIG. 16A depicts a handle at the proximal end of a ligating device in a fifth position.
Figure 16B:
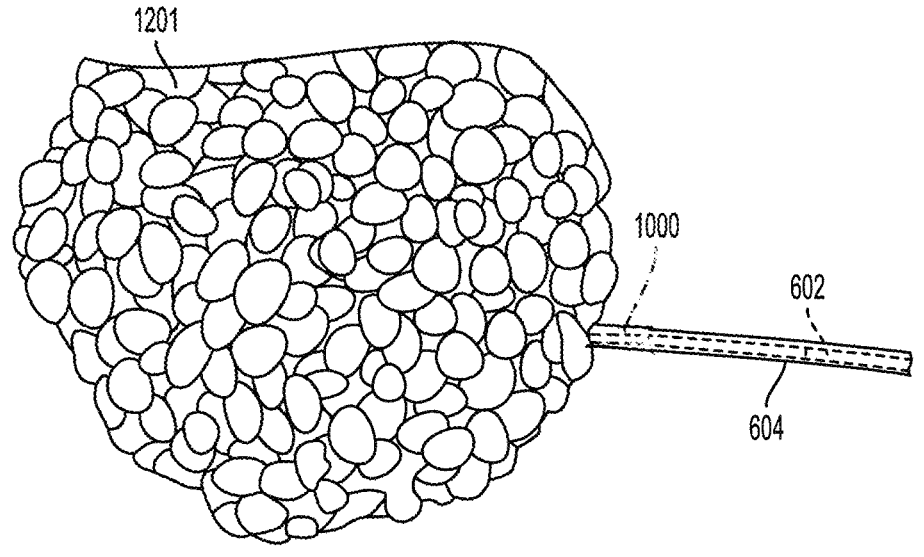
FIG. 16B depicts a loop extended from a distal end of a catheter sheath in a position corresponding to the position of the device in FIG. 16A.

When the cinch component 1000 is fully engaged, the loop is locked into position. In FIG. 16A, the spool is advanced distally on the rail handle. In FIG. 16B, the loop is locked around the tissue 1201, and the cinch being fully engaged means that the loop is irreversibly tightened. When the cinch is activated, the cinch slides over the proximal portion of the loop, trapping the loop inside the distal portion of the cinch so that the remaining length of loop distal to the cinch is kept at the required size to provide constant pressure to target tissue. The proximal portion of the cinch that covers the hook with the loop on it when in an unengaged state, is now moved off of the hook. When this occurs, the hook, with the loop still attached, is positioned such that it is inside the pusher tube 602. This ensures that the loop is not yet released from the hook. Other exemplary embodiments can include other mechanisms of maintaining the loop on the hook until deployment is desired. The sliding engagement of the cinch tightens the loop around the polyp or other tissue to be ligated. Thus when the cinch is engaged and the hook with loop attached are in the pusher tube, the loop is cinched, preferably around the desired tissue.

Figure 17A:
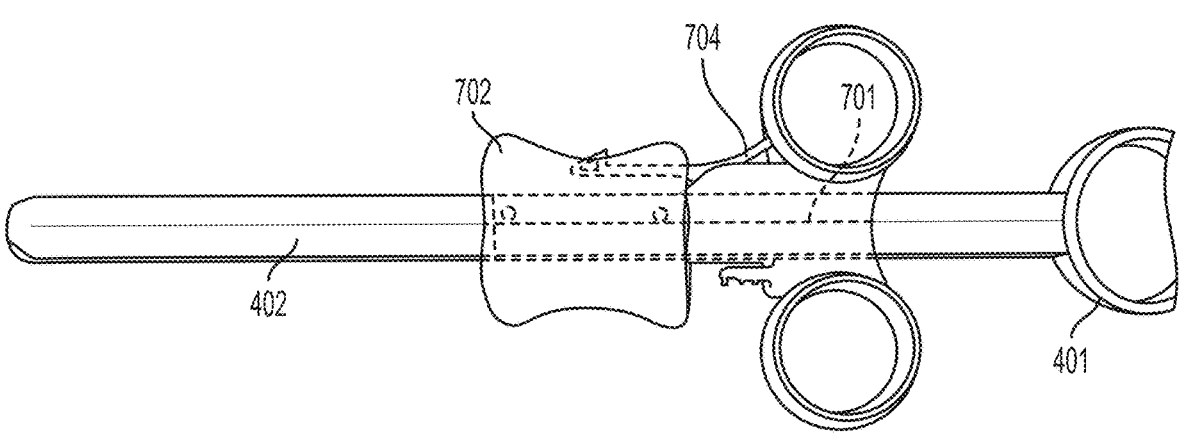
FIG. 17A depicts a handle at the proximal end of a ligating device in a sixth position.
Figure 17B:
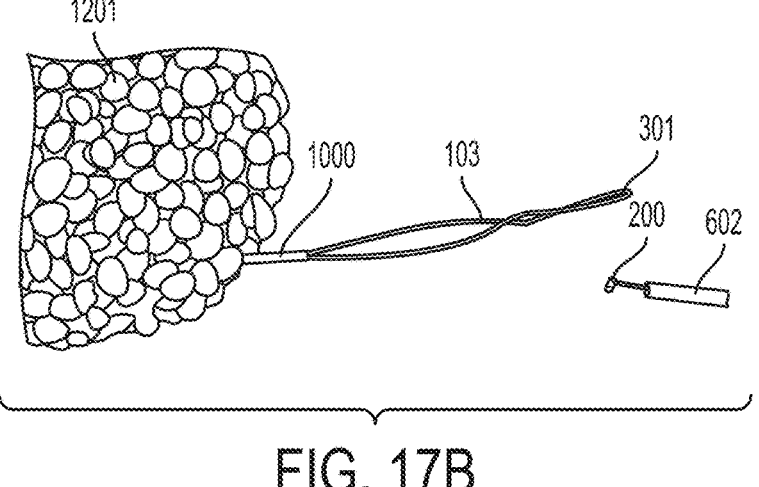
FIG. 17B depicts a loop extended from a distal end of a catheter sheath and released from the hook in a position corresponding to the position of the device in FIG. 17A.

FIGS. 17A and 17B illustrate the proximal and distal ends of the ligating device, respectively, when the loop and cinch are released from the catheter. FIG. 17A illustrates that the spool and ring handle are reconnected to each other. The spool 702 is moved back in a proximal direction along the handle rail 402 until it is reconnected with the ring handle 701, and the proximal movement of the spool is what pulls the pusher tube back in a proximal direction. This proximal movement of the pusher tube causes the loop to be released, because it exposes at least a distal portion of the hook from its distal end. This releases the loop from the handle, because the loop is no longer held in place on the hook by the pusher tube. Connecting the spool back together with the ring handle releases the loop from the handle because the irreversible cinching has already occurred, as described above. The movement of the pusher tube causes the loop and cinch to be released from the catheter, as illustrated in FIG. 17B. The catheter sheath 604 can then be withdrawn, and the loop and cinch remain tightened around the tissue 1201. The hook does not need to extend distally from the catheter sheath to be released from the loop. The loop is released whether or not you extend the hook from the catheter sheath, as it is the cinch component that provides a retaining function and prevents premature separation of the hook and loop while the hook is still within the cinch component. The cinch component 1000 remains with the loop 103.

In another exemplary embodiment, a clip 1801 can be integrated onto the cinch component in place of a ligating loop. The clip can be a hemostatic clip, but is not limited thereto. The clip can be made of one or more materials, including but not limited to a polymer, metal, glass, or ceramic. The metal can be a biocompatible metal alloy, and/or it can be a non-ferrous material. The clip can be for example, stainless steel, titanium, or an alloy thereof.

Figure 18A:
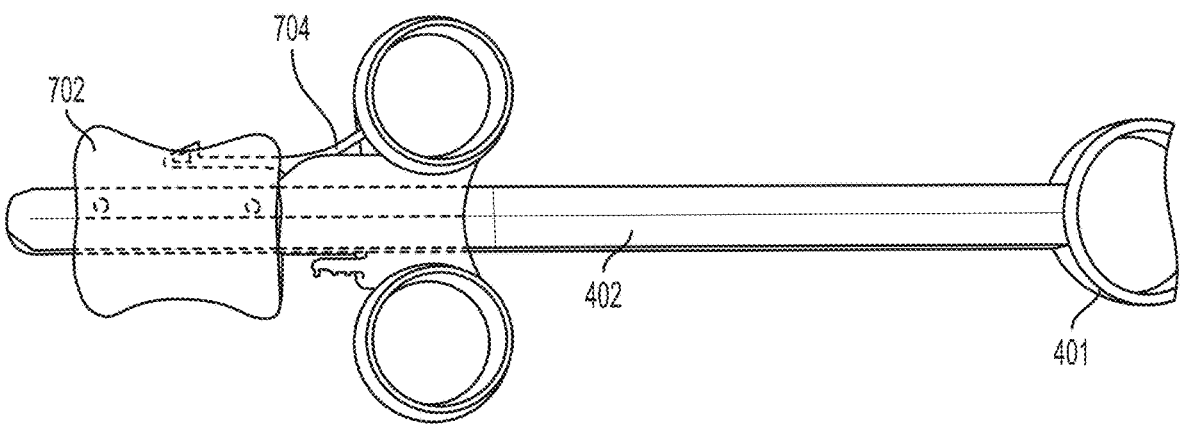
FIG. 18A depicts a handle at the proximal end of a ligating device in a first position.

FIGS. 18A-22B illustrate the use of the actuator apparatus with a clip and how the components are fit together. The assembly operates similarly to the ligating assembly having a loop on the distal end as described above. FIGS. 18A and 18B illustrate the clip 1801 extended from catheter sheath 604 and the relative positioning of the actuator assembly components at the proximal end. FIG. 18A illustrates the proximal end of the ligating device 100. In FIG. 18A, the ring handle 701 and the spool 702 are connected to each other, and are spaced apart from the proximal ring 401, by a distance. The movement of the spool 702 and ring handle 701 in a distal direction causes the clip 1801 in FIG. 18B to be extended from the catheter sheath 604, and to be in a fully open position when extended from the catheter sheath. In FIG. 18B, the clip 1801 is extended distally from the catheter sheath 604. This distal movement of the spool and ring handle together pushes the clip 1801 in a distal direction out of the catheter so that it opens and can be positioned around tissue that is intended to be held together by the clip, as illustrated in FIG. 18B. Moving the spool and ring handle in a proximal direction along the handle rail 402 retracts the clip 1801 back within the catheter sheath 604. The cinch component 1000 moves with the clip at this stage; that is, the cinch component is not moving over the clip to irreversibly tighten it. The spool 702 and ring handle 701, when they are connected, can be moved proximally and distally as many times as the user desires to adjust the extension of the clip from the distal end of the catheter sheath, and to assist with positioning the clip.

Figure 18B:
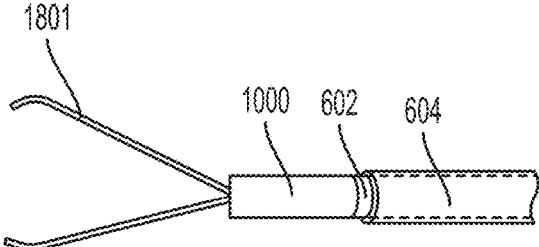
FIG. 18B depicts a clip extended from a distal end of a catheter sheath in a position corresponding to the position of the device in FIG. 18A.
Figure 19A:
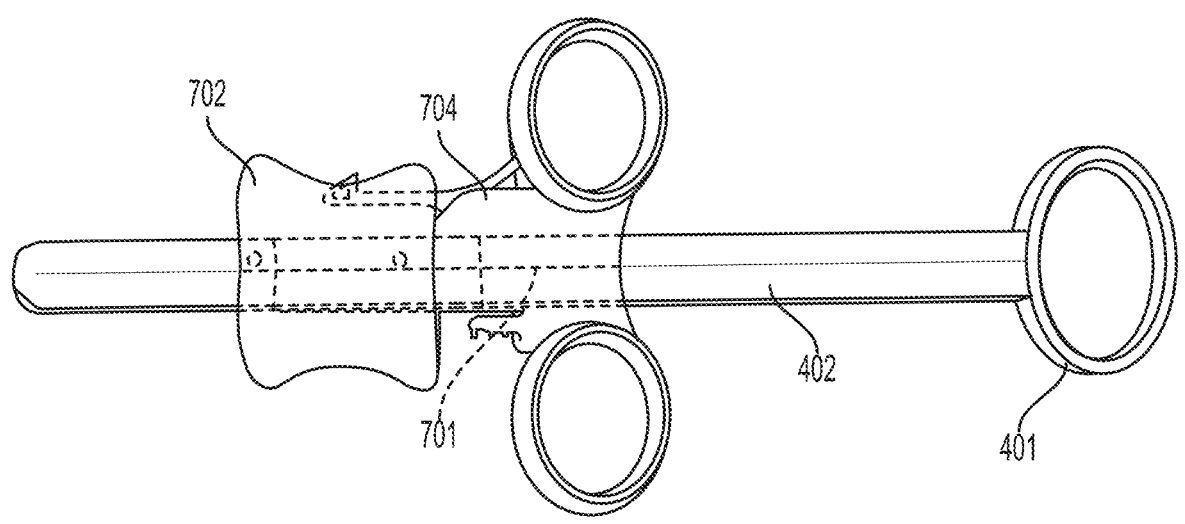
FIG. 19A depicts a handle at the proximal end of a ligating device in a second position.
Figure 19B:
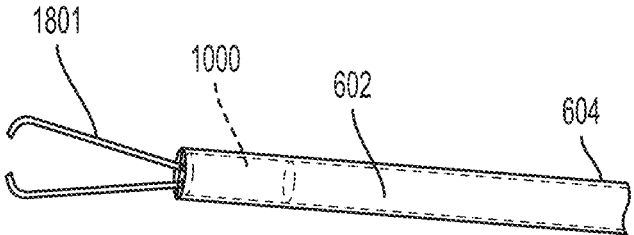
FIG. 19B depicts a clip extended from a distal end of a catheter sheath in a position corresponding to the position of the device in FIG. 19A.

FIGS. 19A and 19B illustrate the proximal and distal ends, respectively, of the ligating device 100 when the spool and ring handle are more proximally located on the handle rail than in FIGS. 18A and 18B. FIG. 19A illustrates the spool 702 connected to the ring handle 701 and positioned closer to the proximal ring 401 than is illustrated in FIG. 18A. FIG. 19B shows the corresponding clip 1800, with at least a portion of the clip retracted into the catheter sheath.

Figure 20A:
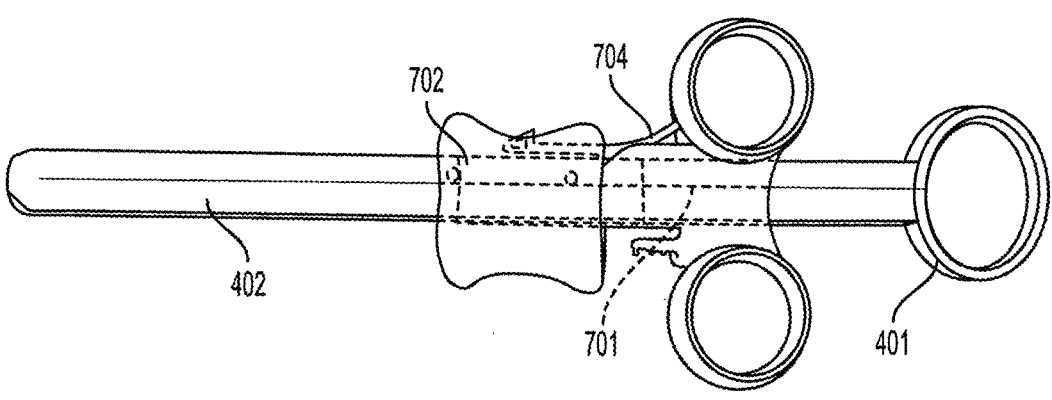
FIG. 20A depicts a handle at the proximal end of a ligating device in a third position.
Figure 20B:
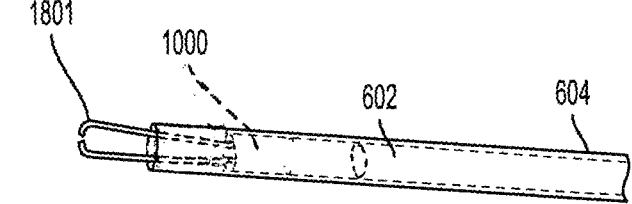
FIG. 20B depicts a clip extended from a distal end of a catheter sheath in a position corresponding to the position of the device in FIG. 20A.

FIGS. 20A and 20B illustrate the ligating device 100 when the spool and ring handle are moved even farther in a proximal direction, toward the ring handle 701. FIG. 20A illustrates the proximal end of the ligating assembly 100 and illustrates the spool 702 and ring handle 701 still together. FIG. 20B illustrates the position of the clip 1801 that corresponds to the spool and ring handle position of FIG. 20A. In use, the clip in this position would be closed around tissue holding two portions of tissue together. The spool and ring handle can be moved in a proximal direction until a distal portion of the catheter sheath 604 is covering the clip sufficiently so that the clip is deemed closed. In this position, when the catheter sheath is covering the clip, the clip is fully closed to simulate how the clip will be irreversibly closed when the cinch component is used to irreversibly close the clip. A desired tightness can be one that restricts blood flow to the tissue surrounded by the clip. The proximal movement of the spool pulls the pusher tube and therefore the cinch in a proximal direction, and the proximal movement of the ring handle pulls the drive wire, hook, and therefore clip back towards and/or into the catheter sheath, causing the clip to start moving from an open configuration to a closed configuration.

Figure 21A:
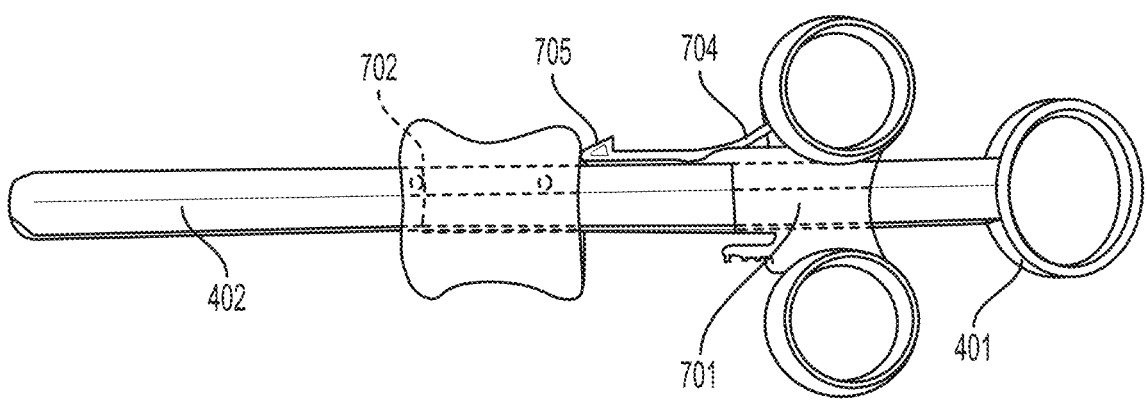
FIG. 21A depicts a handle at the proximal end of a ligating device in a fourth position.

When the cinch component 1000 is fully engaged, the clip is cinched shut. In FIG. 21A, the spool is advanced distally, separate from the ring handle, along the handle rail. The physical size differences and operational envelopes of the loop and clip embodiments will likely necessitate different travel distances and possibly different handle lengths to accomplish cinching.

Figure 21B:
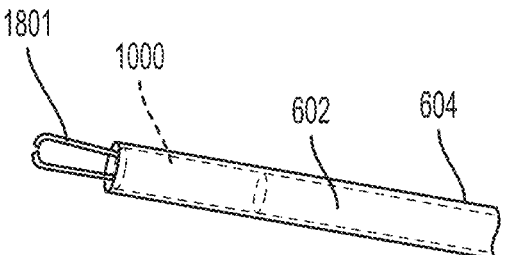
FIG. 21B depicts a clip extended from a distal end of a catheter sheath in a position corresponding to the position of the device in FIG. 21A.

In FIG. 21B, the clip is irreversibly locked in a closed position, clipping together tissue. When the cinch component is activated, the cinch component slides over a central portion of the clip, to irreversibly hold the legs of the clip closed. The proximal portion of the cinch that covers the hook at the proximal end of the clip when in an unengaged state, is now moved off the hook. When this occurs, the hook with the clip still attached, is positioned such that it is inside the pusher tube 602. This ensures that the clip is not yet released from the hook until the operator has sufficiently tightened the clip on the tissue. The sliding engagement of the cinch component tightens the clip around the designated tissue. Thus, when the cinch component is engaged and the hook with clip attached are in the pusher tube, the clip is in a closed configuration, having its legs close enough together to hold tissue together or clamp tissue to stop blood flow.

Figure 22A:
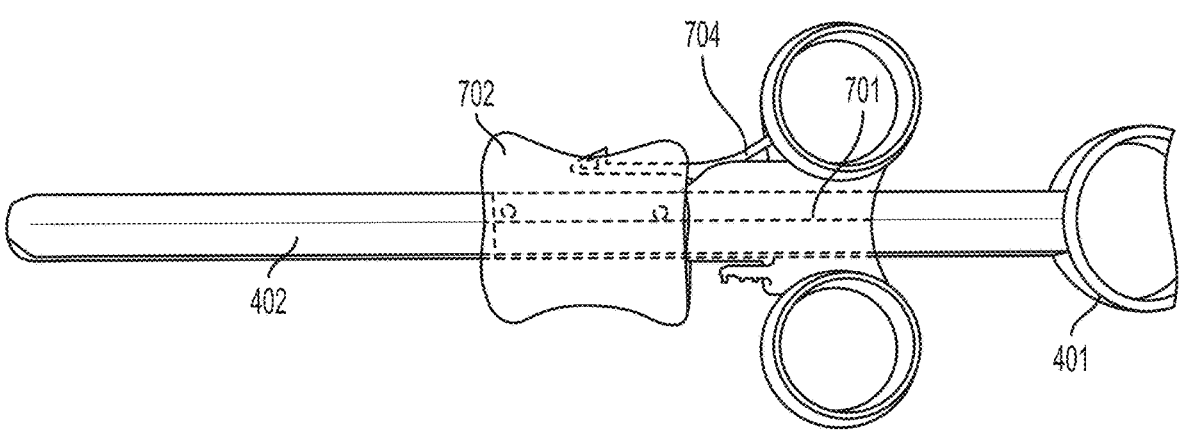
FIG. 22A depicts a handle at the proximal end of a ligating device in a fifth position.
Figure 22B:
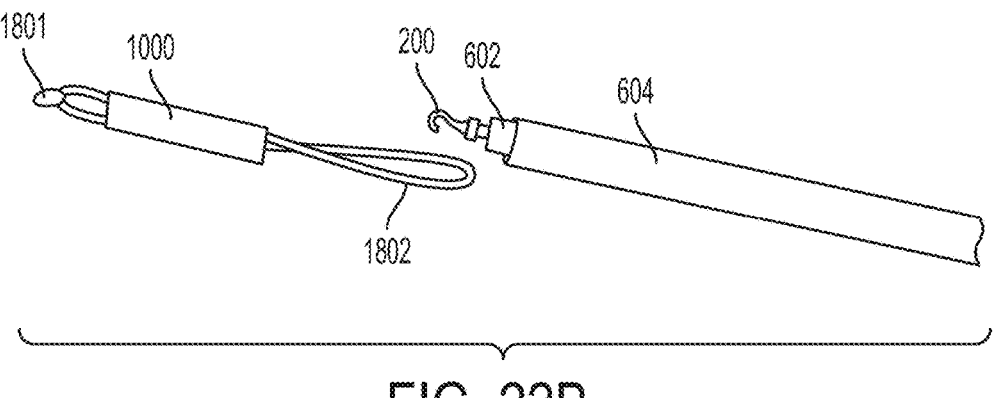
FIG. 22B depicts a clip extended from a distal end of a catheter sheath in a position corresponding to the position of the device in FIG. 22A.

FIGS. 22A and 22B illustrate the proximal and distal ends of the ligating device, respectively, when the clip and cinch release from the catheter. FIG. 22A illustrates that the spool and ring handle are reconnected to each other. The spool 702 is moved back in a proximal direction along the handle rail 402 until it is reconnected with the ring handle 701. The clip is released when the pusher tube is pulled back proximally, exposing at least a distal portion of the hook and clip extending from its distal end. This is achieved by the user moving the spool such that it reconnects with the ring handle. This connection releases the clip from the handle, because the clip is no longer held in place on the hook by the pusher tube. This reconnection causes the clip and cinch to be released from the catheter, as illustrated in FIG. 22B. The catheter sheath 604 can then be withdrawn, and the clip and cinch remain tightened around the tissue. The cinch component 1000 remains with the clip 1801.

In an exemplary embodiment, the cinch component can have features that allow for housing and movement of clip arms. The cinching portion can also have features that allow for the locking of clip arms once they are brought to their most proximal position within the cinch. These features are illustrated in FIGS. 23A-26E.

Figure 23A:
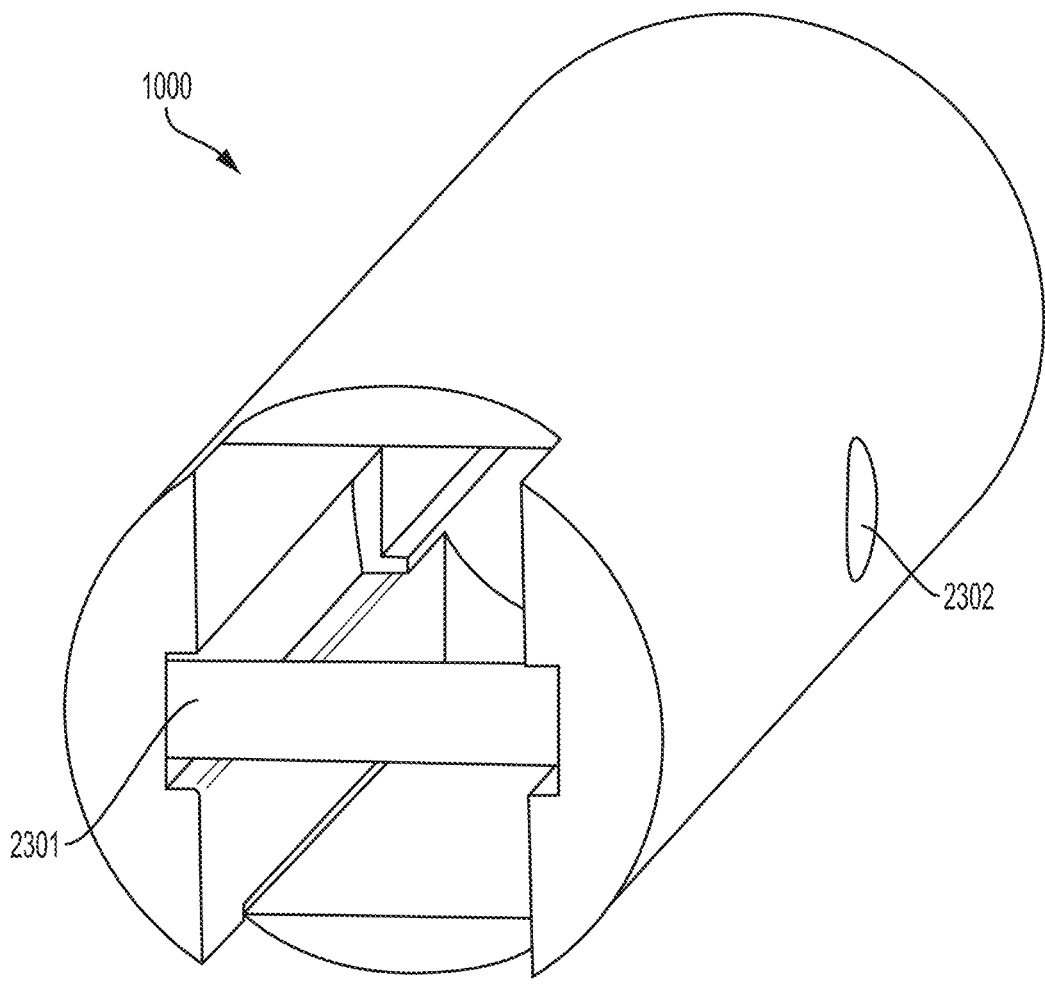
FIG. 23A shows an alternative view of a cinch with features adapted for operation of a clip.

FIG. 23A illustrates an isometric front view of a cinch component 1000. This exemplary embodiment of cinch component can have a substantially cylindrical shape, with side opening 2302 and crossbar 2301. There can be one side opening or there can be two side openings, one on each side of cinch component. A side opening 2302 can extend from the exterior of the cinch component towards a bore 2303 extending longitudinally through the cinch component. The distal portion of the cinch can have a cross bar 2301 to prevent excessive distal movement of clip arms and to provide a camming surface to help force the clip arms open when they are moved distally outwards from the cinch. The crossbar can be made of a piece of material fit into an opening of the distal end of the cinch component such that it extends across the opening of the distal end of the cinch component. In another exemplary embodiment, the crossbar can be made of tabs that extend from the main piece of the cinch component that are bent over to form the cross-bar.

Figure 23B:
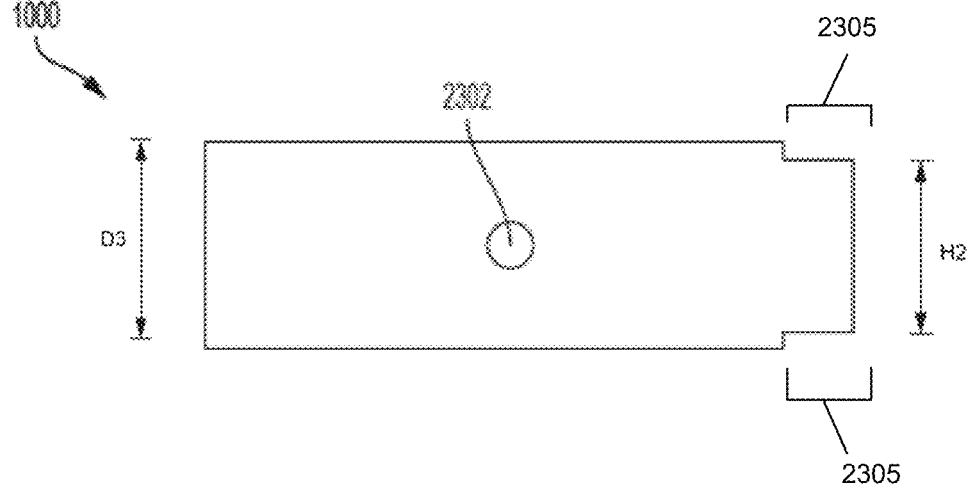
FIG. 23B depicts a cinch with features adapted for operation of a clip.
Figure 23C:
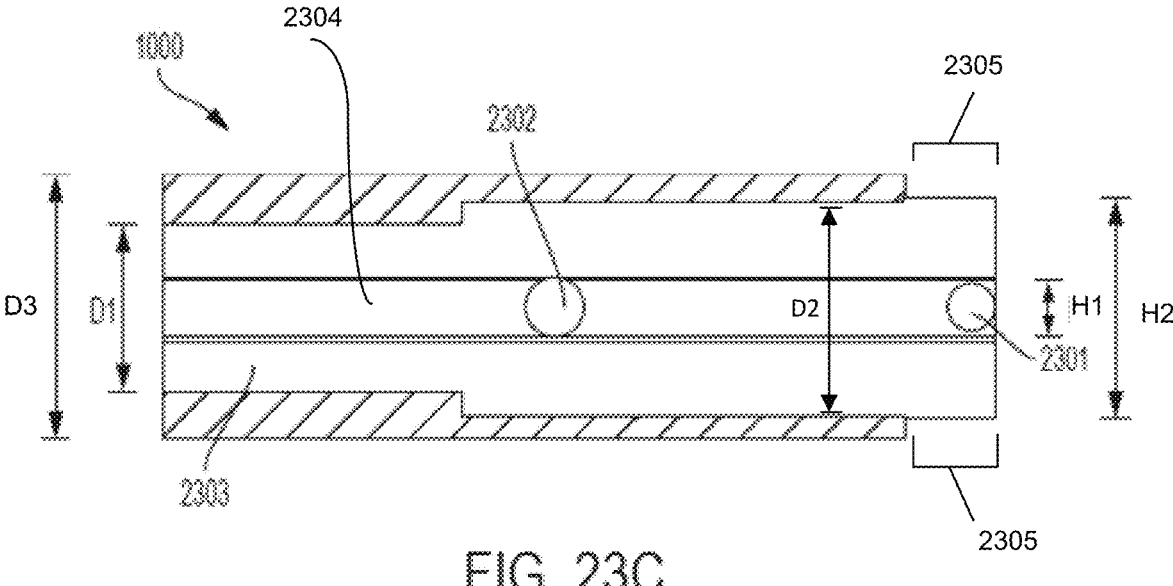
FIG. 23C shows a cross-section of a cinch with features adapted for operation of a clip.

FIG. 23B illustrates a side view of the cinch component of FIG. 23A. Here, the side opening 2302 is aligned with another side opening on the other side of the cinch component 1000. FIG. 23C illustrates a cross-section view of the cinch component of FIGS. 23A and 23B. Bore 2303 extends longitudinally through the cinch component. In this exemplary embodiment, the outer and inner (bore) diameters of the cinch component 1000 vary. The bore 2303 can have a proximal inner diameter D1 sufficient in size to accommodate a hook 200 and proximal end of a tether 2400. The bore can have a distal inner diameter D2 sufficient in size to hold a distal portion of tether 2400 and two clip arms 2501 and 2502. The cinch component can have an outer diameter D3, sized to fit in a catheter sheath 604. H1 represents the height of interior cutout 2304, which is sized to accommodate the width of the clip when it is inside the cinch component. There can be an interior cutout 2304 on each side of the interior of the cinch component. The height of the interior of the cinch component, H2, is sized to permit a clip to fit within the cinch component 1000. The height H2 can also be a diameter, because the cutout can be circular. This volume is created by cut portions 2305 which create room for the clip arms to fit inside the cinch component 1000. The proximal outer diameter D3 can extend farther distally than the proximal inner diameter D1. Side opening(s) 2302 can be positioned such that they are in the region of the cinch component having inner diameter D2 and outer cinch diameter D3. Crossbar 2301 can be at the distal end of the cinch component.

Figure 24:
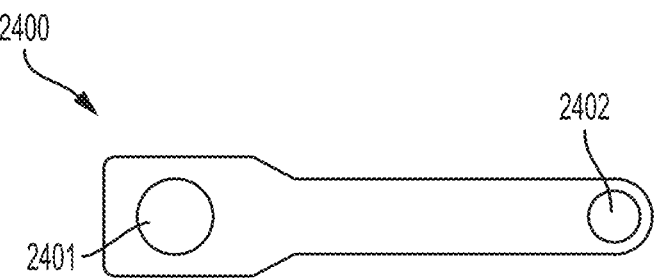
FIG. 24 depicts a tether to link the clip to the hook in accordance with an exemplary embodiment.
Figure 25:
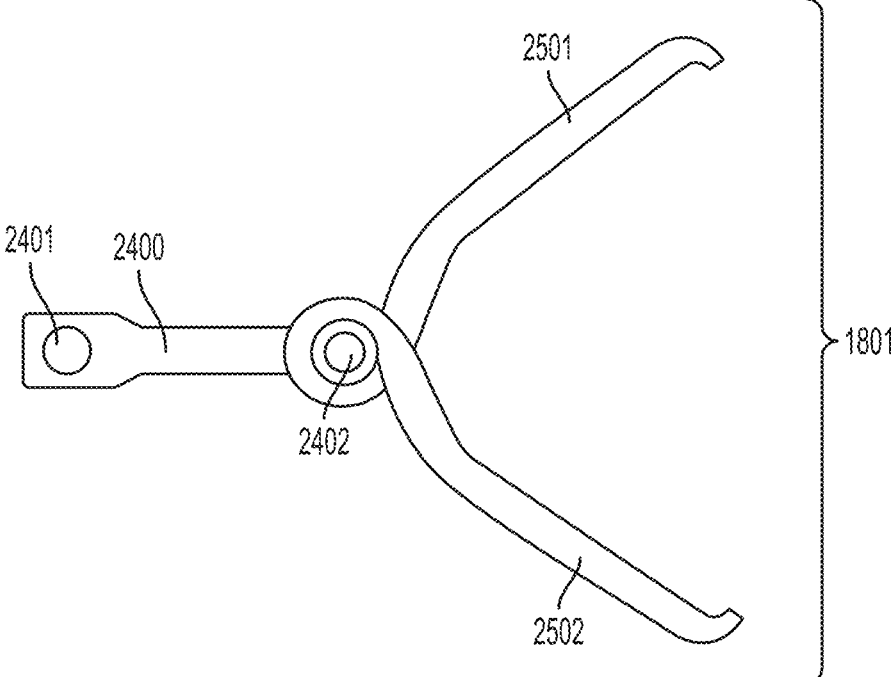
FIG. 25 depicts a tether and clip in accordance with an exemplary embodiment.

FIG. 24 illustrates a tether 2400 that can be used to hold clip 1801 on the hook 200 until a user is ready to cinch and deploy the clip 1801. The clip of the exemplary embodiment illustrated in FIG. 25 can be made of two separate pieces having clip legs 2501 and 2502. The tether can have a proximal end and a distal end, and the proximal end can be larger than the distal end. The proximal end of the tether can have a proximal opening 2401 and a distal protrusion 2402. The proximal opening 2401 can be circular and can extend through the tether. Alternatively, the proximal portion of the tether may form one half of a releasable couple with the hook 200 forming the other half. The two halves of the releasable couple have a railroad coupler configuration, or a "handshake" configuration, where the proximal portion of the tether and the hook each form one "hand." The proximal opening of the tether is of a size and shape sufficient to fit the tether on the distal end portion 204 of hook 200 so that tether and hook remain connected when inside cinch component, and also to allow the tether to slip off the hook when the cinch component is removed from overlapping the hook. The distal protrusion 2402 on the tether can be circular and can extend outward from opposing sides of the tether. The distal circular protrusion 2402 can be of a size and shape to fit in between the proximal ends of clip legs 2502, and also extend far enough outward from the tether to pass through side openings 2302 of the cinch component when aligned with the side openings. The protrusions 2402 of tether 2400 may be of an elastic character, or otherwise spring loaded, so as to extend into openings 2302 when clip 1801 is withdrawn into cinch component 1000. Such extension may be within, equal to, or just outside of the outer diameter D3 of the cinch. In this embodiment the interaction of distal circular protrusion 2402 and side opening(s) 2302 provides the primary retaining force that keeps the clip closed on tissue in contrast to other embodiments where the friction between the cinch and the clip or loop provides the primary retaining force. The tether can be pulled all the way inside the cinch before locking occurs. The resistance between the tether and the cinch can be enough so that the cinch holds the tether in place but great enough to cause the tether to be pushed over when a pushing force is applied to it. In an alternative embodiment, protrusions 2402 may be inelastic and interact with openings 2302 that are formed from elastic tabs or sections of hypotube. In this case the retaining force is in effect once the protrusions are moved proximally over the elastic tabs and the tabs spring back into position to prevent distal movement of the protrusions.

The tether of FIG. 24 is merely one exemplary embodiment and the structure of the tether can take one of other forms of a size and shape to fit within the cinch component.

Figure 26A:
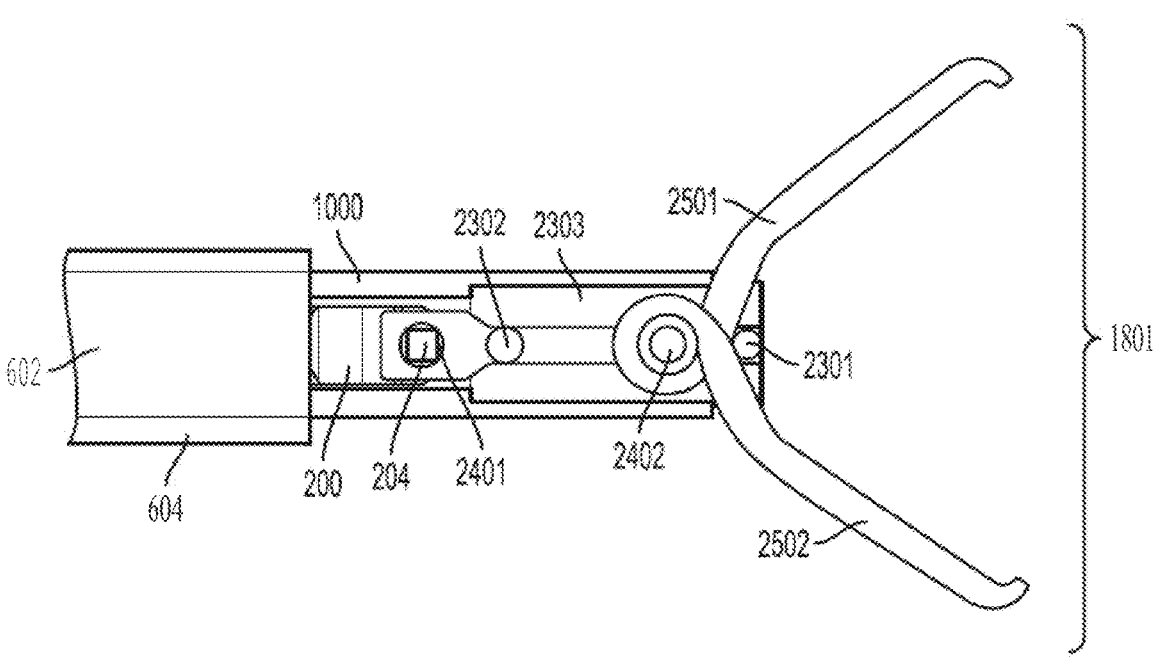
FIG. 26A depicts an alternative embodiment of a clip in a position corresponding to the position of the device in FIG. 18A.

FIGS. 26A-26E illustrate the various positions of the exemplary embodiments in FIGS. 23A-25 as it is positioned and cinched. In FIG. 26A, the proximal end of the cinch component 1000 is adjacent to a distal end of the pusher tube 602. The cinch component can be releasably connected to a distal end of a pusher tube. The cinch and pusher tube can be adjacent to each other but are not required to be connected. A loose connection between them can transmit rotational movement should the use of the device benefit from having rotational movement of the cinch. A connection between the pusher tube and cinch can be under torque, and releasable axially. For example, a slot-and-tab connection, where the axial movement of pusher tube and cinch relative to each other separates the pusher tube and cinch, but rotation of one relative to the other can connect and detach the pusher tube and cinch.

Pusher tube 602 is inside catheter sheath 604 and the cinch component 1000, tether 2400, and clip 1801 have been extended distally out of the catheter sheath. The tether 2400 is connected to the hook 200 by having the distal end portion of the hook inserted through the proximal opening 2401 of the tether. The hook and tether are positioned in the proximal portion of the bore having proximal internal diameter D1. The distal elongate portion of the tether is within distal portion of the bore having distal internal diameter of D2. The proximal end of the clip 1801 is connected to the tether because the distal protrusion 2402 extends through the proximal portion of the clip. The cross-bar 2301 helps to hold the clip in place connected to the tether and cinch component. Clip legs 2501 and 2502 are in an open configuration that can be used to position the clip around tissue.

Figure 26B:
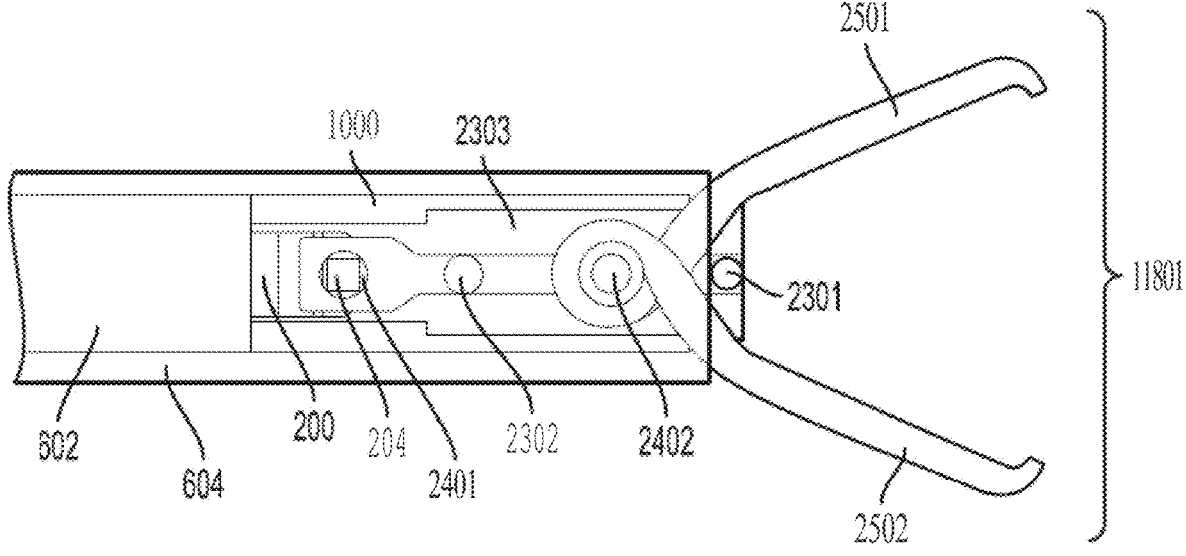
FIG. 26B depicts an alternative embodiment of a clip in a position corresponding to the position of the device in FIG. 19A.

FIG. 26B illustrates the cinch component 1000 retracted at least partially into the catheter sheath 604. In FIG. 26B, all but a distal portion of the cinch component 1000 is within the catheter sheath, except for the portion having the crossbar. Enough of the cinch is retracted such that the tether is fully retracted within the catheter sheath. The clip 1801 is in a partially closed position. The cinch and clip can be moved between the fully open position of FIG. 26A and the partially closed position of 26B as many times as needed to properly position the clip. The tether is still connected to the hook. Upon opening and/or reopening the clip, the crossbar 2301 acts as a camming surface and applies force to the interior surface of clip legs 2501, 2502, pushing them open as the clip is pushed distally.

Figure 26C:
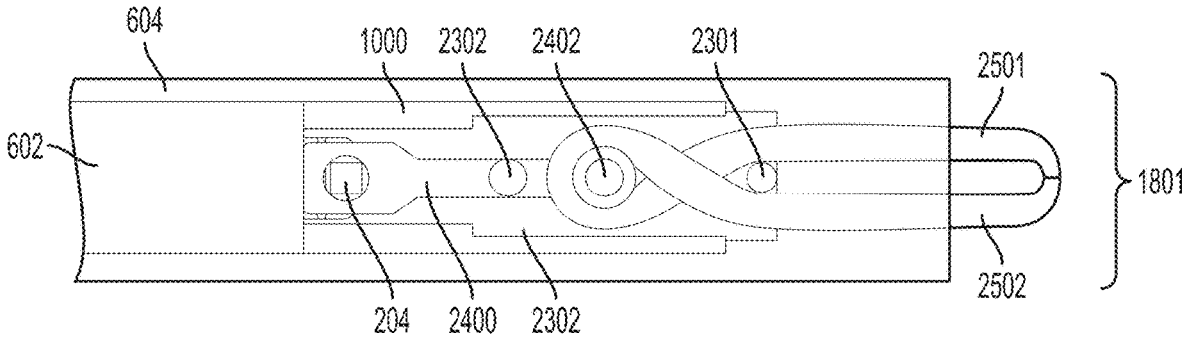
FIG. 26C depicts an alternative embodiment of a clip in a position corresponding to the position of the de vice in FIG. 20A.

FIG. 26C illustrates the cinch component and tether fully retracted within the catheter sheath. The hook is shown partially retracted into the pusher tube, but is not required to be retracted into the pusher tube. The tether is connected to the hook. The clip is partially retracted into the catheter sheath. The tether remains connected to the clip throughout the positioning and deployment process, and along with the cinch component, remains with the clip once the clip is discharged from the catheter. In FIG. 26C, the clip is still reversibly closed because the distal circular protrusions 2401 on the tether have not yet been fit into the side openings 2302 on the cinch component.

Figure 26D:
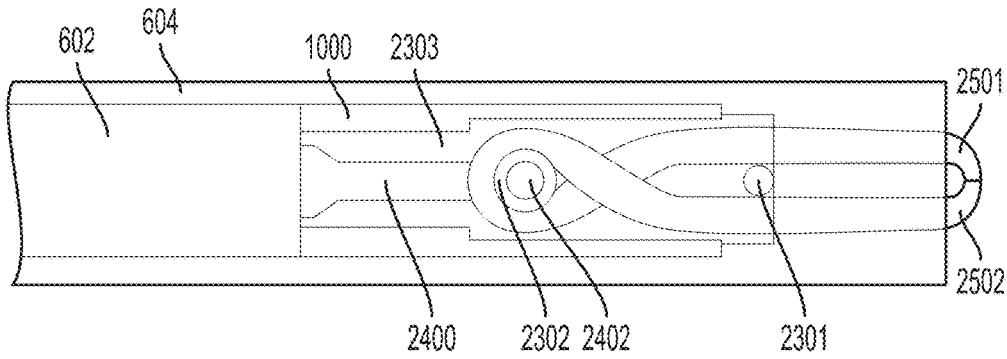
FIG. 26D depicts an alternative embodiment of a clip in a position corresponding to the position of the device in FIG. 21A.

FIG. 26D illustrates the clip in an irreversibly closed position. In FIG. 26D, the hook is not visible because it is retracted within the pusher tube 602. The hook is within the pusher tube because it was pulled proximally by the drive wire (not shown). In this position, the distal protrusion 2402 of the tether is press-fit within the cinch component's side opening 2302, which locks the tether in place, irreversibly cinching the clip which has been pulled into the cinch component because of its connection to the tether. The hook, tether, and clip have all been pulled proximally by the drive wire.

Figure 26E:
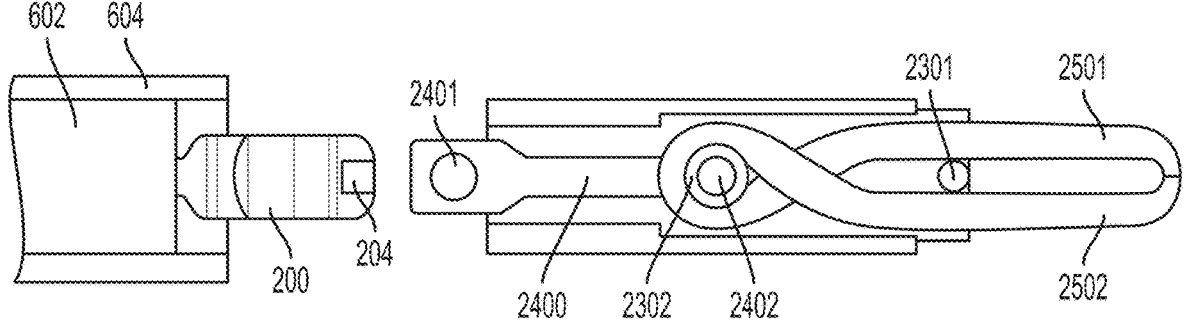
FIG. 26E depicts an alternative embodiment of a clip in a position corresponding to the position of the device in FIG. 22A.

FIG. 26E illustrates the clip, cinch, and tether no longer attached to the hook. In this position, the hook has been moved distally again, to extend at least partially outward beyond the distal end of the catheter sheath. The hook is extended out past the catheter sheath a sufficient amount to release the distal end portion 204 of the hook from the proximal opening 2401 of the tether. The hook has been moved in a distal direction by moving the ring handle 701 in a distal direction. The tether remains on the hook when the hook is in the cinch. When the pusher tube is advanced and pushes the cinch forward along the clip arms, the hook and tether connection is moved proximally within the pusher tube, where they remain connected. This prevents the device from being released before it is fully tightened by the cinch. Once the hook and proximal end of the tether are no longer contained by either the cinch component or the pusher tube, the tether is free to be removed from the hook. In the position illustrated in FIG. 26E, the clip 1801 is irreversibly closed, and the assembly of the cinch, tether, and clip have been discharged from the catheter sheath, to be left in place on the tissue it is clipped on (tissue not shown). In other embodiments the protrusion can have spring-like properties, so that the clip may be un-cinched through compression of the protrusions 2402 in the case where their interaction with 2302 is the primary retaining force acting on the clip. Compression of the protrusions can be accomplished by using forceps or a snare in such an embodiment.

Figure 32:
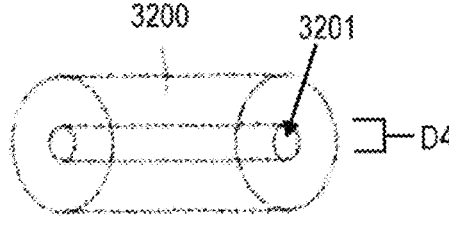
FIG. 32 illustrates a cinch component according to an exemplary embodiment of a ligating device.

In another exemplary embodiment, the loop (or clip) can be released from the hook when the hook has been pushed out the distal end of the pusher tube. This differs from the embodiments described above because the loop (or clip) is prevented from moving off the hook by the interior wall of the pusher tube, rather than the interior wall of the cinch component. In this embodiment, the cinch component can be of one piece, and can have a constant inner diameter along the entire length of the cinch. FIG. 32 illustrates an exemplary embodiment of a cinch component 3200 having bore 3201 extending therethrough with a constant inner diameter, D4. The inner diameter of the bore 3201 of cinch component 3200 is small enough to hold two strands of the proximal portion of the loop 103 and to remain in place once moved in a distal direction along the loop to cinch it.

FIGS. 34A-37 illustrate the additional exemplary embodiment of the ligating device, which include the cinch component 3200 with a constant inner diameter bore and snap clip 3300 as described above. In this embodiment the detachment of the hook is determined by when the hook is pushed distally through the distal end of the pusher tube. The features of this embodiment and the previously described embodiment features are interchangeable with each other. The snap clip used to connect the spool and ring handle together in the following embodiment can also be used with the cinch component 1000 in the above-described embodiments to detach the hook from the loop. Likewise, the embodiments having a button on the spool can also be used to detach a hook from a loop cinched with a cinch component having a constant inner diameter bore.

Figure 33:
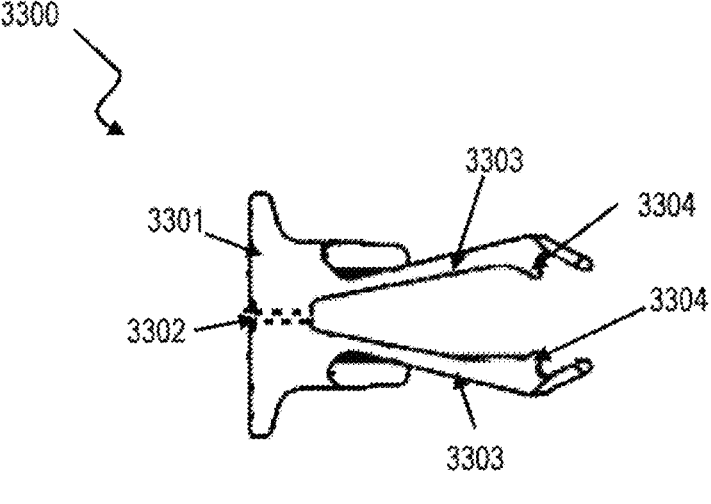
FIG. 33 illustrates a snap clip for connecting a spool to a ring handle in according to an exemplary embodiment of a ligating device.
Figure 34A:
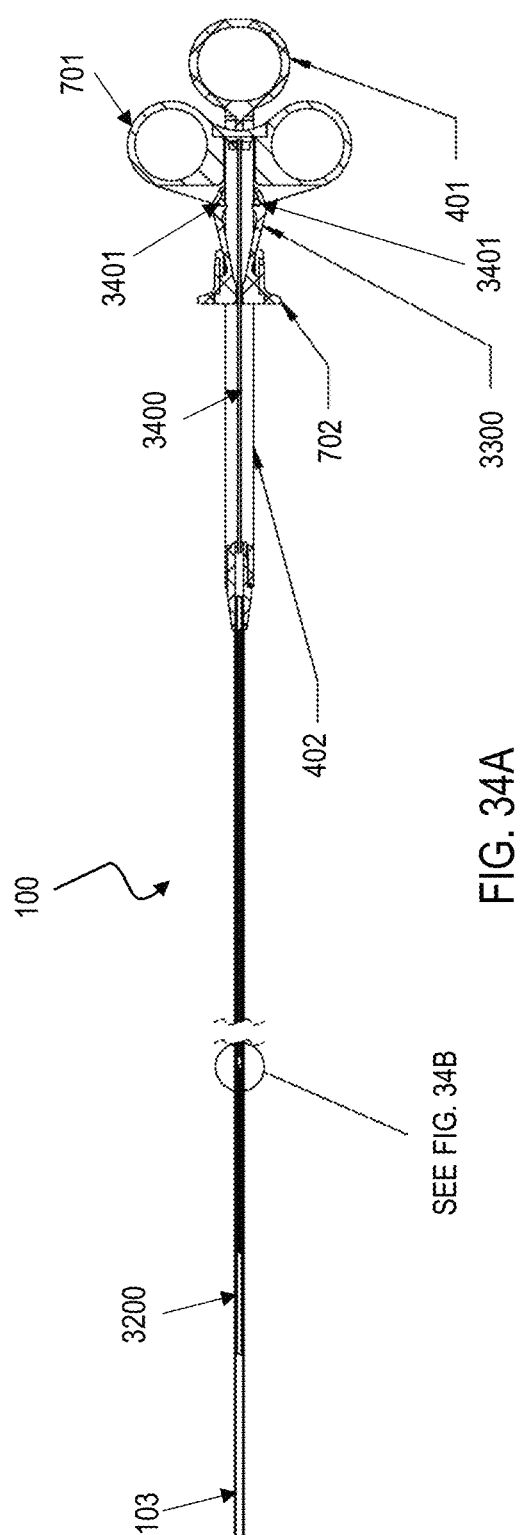
FIG. 34A depicts a ligating device according to an exemplary embodiment with a handle in a first position.
Figure 34B:
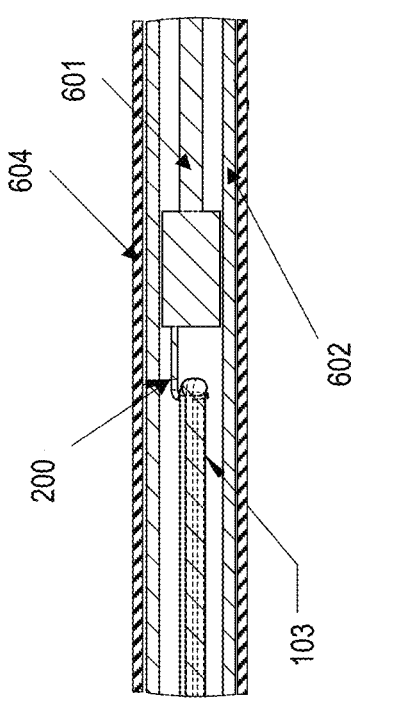
FIG. 34B depicts a portion of a distal end of the ligating device of FIG. 34A in a first position.

FIGS. 34A and 34B illustrate the ligating device 100 in a first position. In this position, the ring handle 701 and spool 702 are connected to each other by a snap clip 3300, and located in a proximal position along the handle rail 402. A close-up of the snap clip 3300 is illustrated in FIG. 33. The snap clip 3300 has a distal base 3301, which is fixedly secured to the spool, and can have a bore therethrough, through which the center rail 3400 of the handle rail can pass through, so that the snap clip is aligned along the rail to guide its movement. The snap clip can have two proximal arms 3303, which expand away from each other to fit onto the ring handle. The proximal arms each have a lip 3304 near their proximal ends that catches onto a corresponding set of protrusions 3401 in the interior of the ring handle. FIG. 34A shows the snap clip in an expanded configuration, latched to the ring handle. In this position, as shown in FIG. 34B, the hook 200, drive wire 601, and proximal portion of the loop 103 are within the pusher tube. The pusher tube 602 is within the catheter sheath 604. The cinch component (see FIG. 34A) can be positioned on the loop near or at the proximal end so that the loop is capable of opening to its greatest position, for positioning around a polyp or other tissue that is to be cinched. In this position, with the spool and ring handle connected to each other, the connected handles can slide along the handle shaft to open and close the loop while maintaining the hook and loop connected to each other. This is because the connection of the spool and ring handle causes the pusher tube to be moved along with the hook and loop, so that the hook cannot become inadvertently exposed. As with the other embodiments described herein, the pusher tube is connected to the spool, and the drive wire and hook, and thus loop and cinch component, are connected to the ring handle. With the spool and ring handle in the connected position, before the cinch component tightens the loop, the pusher tube, loop, hook, cinch, and drive wire can be moved distally and proximally as many times as the user would like, by moving the spool and ring handles, until the desired position is achieved.

Figures 35A, 35B:
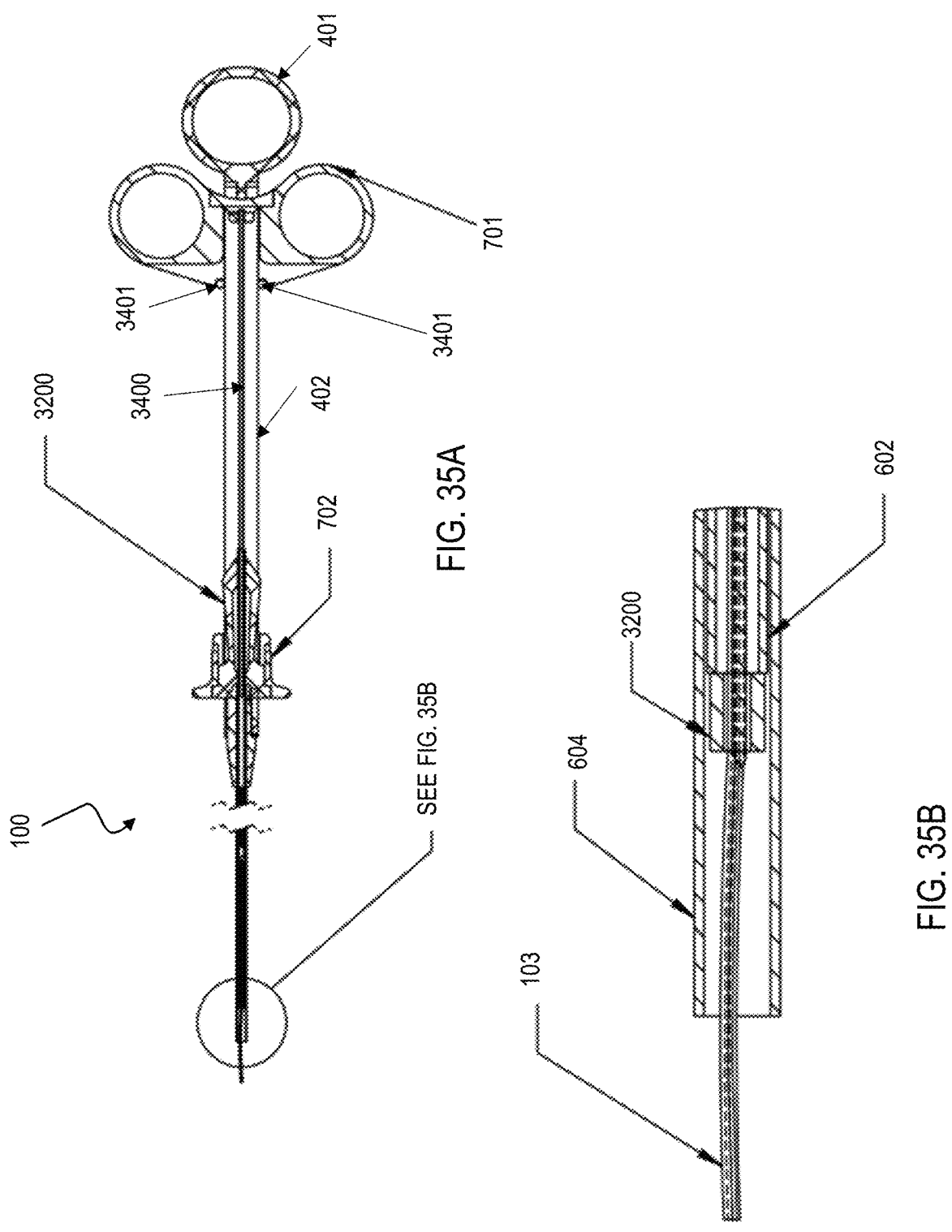
FIG. 35A depicts a ligating device according to an exemplary embodiment with a handle in a second position.
FIG. 35B depicts a distal end of the ligating device of FIG. 35A in a second position.

Referring now to FIGS. 35A and 35B, the ligating device is in a second position. In this position, the spool 702 with snap clip 3300 and ring handle 701 have been separated from each other, and the spool has been moved in a distal direction. The proximal arms 3303 of the snap clip collapse towards each other when separated from the ring handle. By moving the spool in the distal direction, the pusher tube is also moved in a distal direction. The distal end of the pusher tube can contact the proximal end of the cinch component and push it in a distal direction along the loop in order to tighten the loop. FIG. 35A illustrates the position of the spool with snap clip on the handle rail 402 and the position of the ring handle. FIG. 35B illustrates the distal end of the ligating device in this second position. Here, the distal end of the pusher tube 602 is adjacent the proximal end of the cinch component 3200. Both the pusher tube 602 and cinch component 3200 are within the catheter sheath 604. The loop extends from a proximal end within the pusher tube connected to the hook (not shown), through the cinch component, and a distal end extending out past the catheter sheath. The loop can be already positioned around the target tissue when the ligating device is moved to this position. The spool can be moved in a distal direction until the cinch has fully cinched the loop around the target tissue.

Figures 36A, 36B:
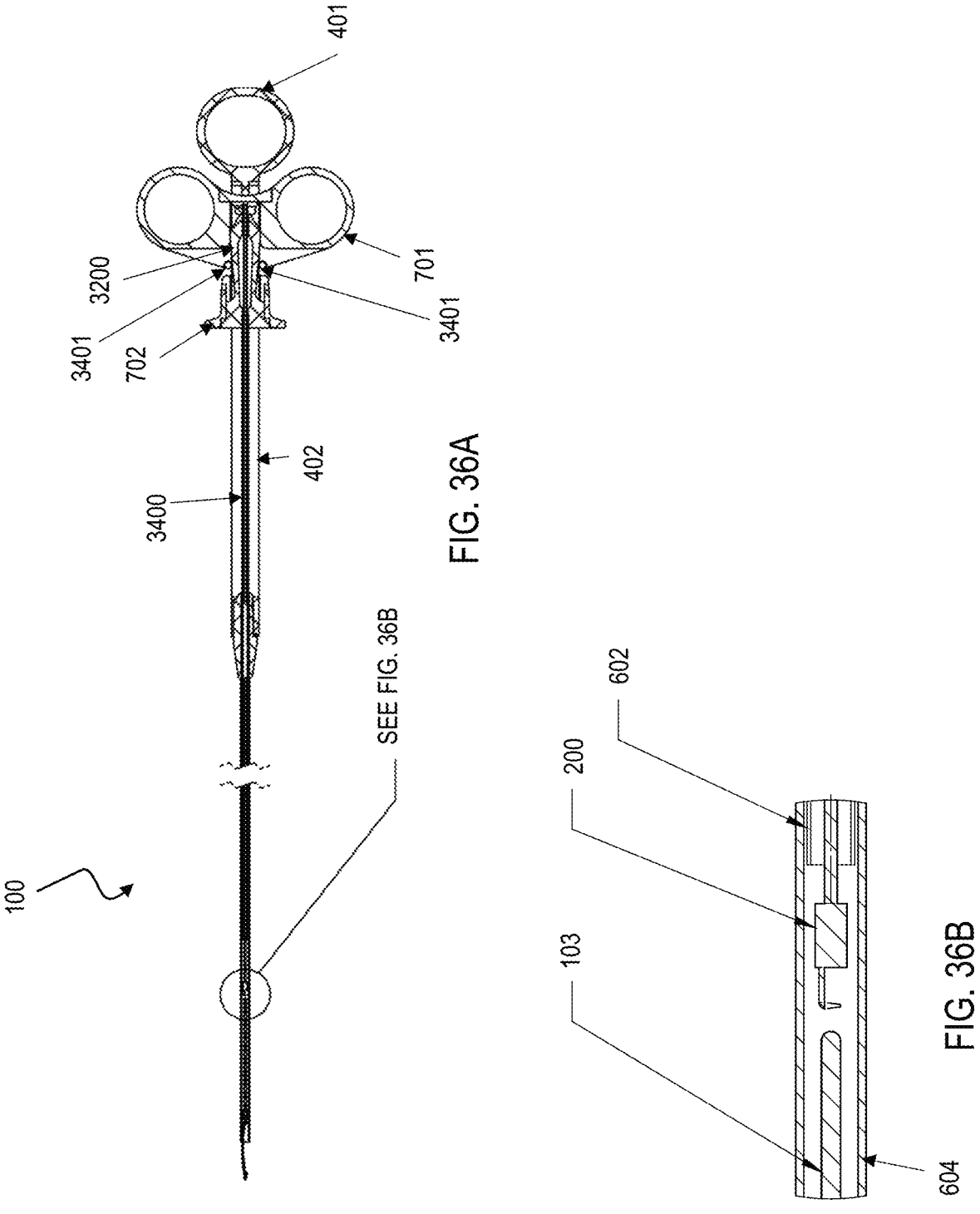
FIG. 36A depicts a ligating device according to an exemplary embodiment with a handle in a third position.
FIG. 36B depicts a portion of a distal end of the ligating device of FIG. 36A in a third position.
Figure 37:
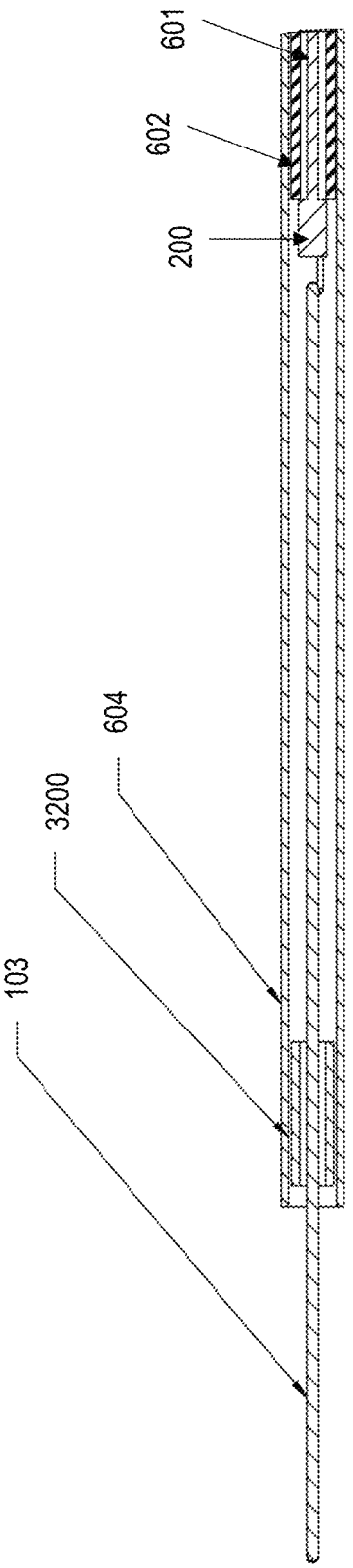
FIG. 37 depicts a loop of the ligating device with the cinch partially actuated and the hook extending out past the pusher tube.

Referring now to FIGS. 36A and 36B, the ligating device is in a third position. In this position, the spool 702 and ring handle 701 are reconnected to each other, with the snap clip 3300, and have been moved to a proximal location on the handle. The spool and ring handle can be connected to each other by moving the spool proximally to the ring handle. To the position shown in FIG. 36A. The proximal movement of the spool towards the ring handle pulls the pusher tube in a proximal direction. This exposes the hook on the loop, and because the pusher tube is no longer restricting the movement of the hook, the loop can be released from the hook. This completes the deployment of the loop around a target tissue. FIG. 37 illustrates the catheter sheath 604 and the cinch component 3200 positioned farther down on the loop 103 to tighten it, in which it is still contained within the sheath. FIG. 37 further illustrates the hook 200 connected to the drive wire 601, where at least the distal end of the hook has been pushed out beyond the distal end opening of the pusher tube 602, but has not yet detached from the proximal end of the loop. FIG. 36B shows the loop 103 released from the hook 200 because they both extend distally past the end of the pusher tube 604. In FIG. 36B, the elements are still contained within the catheter sheath 604.

Accordingly, the various embodiments are not to be limited in scope by the specific embodiments described herein. Further, although some of the embodiments have been described herein in the context of a particular implementation in a particular environment for a particular purpose, those of ordinary skill in the art should recognize that its usefulness is not limited thereto and that the various embodiments can be beneficially implemented in any number of environments for any number of purposes. Accordingly, the claims set forth below should be construed in view of the full breadth and spirit of the embodiments as disclosed herein. While the foregoing description includes many details and specificities, it is to be understood that these have been included for purposes of explanation only, and are not to be interpreted as limitations of the various embodiments. Many modifications to the embodiments described above can be made without departing from the spirit and scope of this description.

What is claimed is:

1. A device for ligating tissue, comprising:
a clip disposed at a distal end of the device and having two clip legs;
a tether having a proximal opening and a distal protrusion, the distal protrusion being operatively coupled to a proximal end of the clip;
a cinch having a bore, a side opening, and a cross-bar disposed distally to a junction of the clip legs;
a hook having a distal end portion configured to be disposed in the proximal opening of the tether;
a drive wire coupled with a proximal end of the hook; and
a pusher tube having a distal end configured to abut a proximal end of the cinch, the drive wire being slidable within the pusher tube;
wherein proximal retraction of the drive wire relative to the pusher tube retracts the clip into the cinch and moves the distal protrusion at least partially into the side opening to irreversibly close the clip.

2. The device for ligating tissue of claim 1, wherein distal extension of the drive wire relative to the pusher tube decouples the hook from the tether when the clip is irreversibly closed.

3. The device for ligating tissue of claim 1, further comprising a catheter sheath, wherein the pusher tube, the drive wire, the hook, and the tether are slidable within the catheter sheath.

4. The device for ligating tissue of claim 1, wherein the clip may be moved between an open position and a closed position before the clip is irreversibly closed.

5. The device for ligating tissue of claim 1, wherein the cross-bar retains the proximal end of the clip in the cinch.

6. The device for ligating tissue of claim 1, wherein a distal portion of the bore of the cinch has a diameter larger than the proximal end of the clip and a proximal portion of the bore of the cinch has a diameter smaller than the proximal end of the clip.

7. The device for ligating tissue of claim 6, wherein the tether is slidable within the proximal portion of the bore of the cinch.

* * * * *